(12) United States Patent
Chandra et al.

(10) Patent No.: US 11,786,571 B2
(45) Date of Patent: Oct. 17, 2023

(54) ORGANOLEPTIC DIETARY PRODUCT FROM FENUGREEK SEED, AND METHOD FOR PRODUCTION THEREOF

(71) Applicant: BIOGEN EXTRACTS PRIVATE LIMITED, Bangalore (IN)

(72) Inventors: Jai Shankar Raghava Chandra, Bangalore (IN); Sujit Mukund, Bangalore (IN)

(73) Assignee: BIOGEN EXTRACTS PRIVATE LTD.

( * ) Notice: Subject to any disclaimer, the term of this patent is extended or adjusted under 35 U.S.C. 154(b) by 41 days.

(21) Appl. No.: 16/786,586

(22) Filed: Feb. 10, 2020

(65) Prior Publication Data

US 2020/0254047 A1 Aug. 13, 2020

(51) Int. Cl.
- A61K 36/48 (2006.01)
- A61K 9/00 (2006.01)
- A23L 33/22 (2016.01)
- B01D 11/02 (2006.01)

(52) U.S. Cl.
CPC .............. *A61K 36/48* (2013.01); *A23L 33/22* (2016.08); *A61K 9/0056* (2013.01); *B01D 11/0288* (2013.01); *A23V 2002/00* (2013.01); *A61K 2236/13* (2013.01); *A61K 2236/15* (2013.01); *A61K 2236/33* (2013.01); *A61K 2236/39* (2013.01); *A61K 2236/51* (2013.01); *A61K 2236/53* (2013.01)

(58) Field of Classification Search
None
See application file for complete search history.

(56) References Cited

U.S. PATENT DOCUMENTS

| | | | |
|---|---|---|---|
| 5,658,571 A | 8/1997 | Gopalan et al. | |
| 5,997,877 A * | 12/1999 | Chang | A23J 1/006 424/757 |
| 6,495,175 B2 | 12/2002 | Rao | |
| 2004/0228932 A1 | 11/2004 | Pilgaonkar | |
| 2005/0084549 A1 * | 4/2005 | Pilgaonkar | A61K 9/7007 424/757 |
| 2010/0247638 A1 * | 9/2010 | Patell | A23L 33/22 424/456 |
| 2013/0071470 A1 | 3/2013 | Aburdeineh | |
| 2018/0256621 A1 * | 9/2018 | Bhaskaran | A61K 31/7048 |

FOREIGN PATENT DOCUMENTS

| WO | WO/1999/025197 | 5/1999 |
|---|---|---|
| WO | WO/2017/046777 | 3/2017 |

OTHER PUBLICATIONS

Chandra et al. (2018) Inter. J. Med. & Health Res. Volume 4, Issue 10: 14-21. (Year: 2018).*
Chevassus et al. (2010) Eur. J. Clin. Pharmacol. 66: 449-455. (Year: 2010).*
Mathern et al. (2009) Phytother. Res. 23: 1543-1548. (Year: 2009).*
Handa et al. (2005) Biosci. Biotechnol. Biochem. 69(6): 1186-1188. (Year: 2005).*
Marlett JA, McBurney MI, Slavin JL; American Dietetic Association. Position of the American Dietetic Association: health implications of dietary fiber. J Am Diet Assoc. 2002;102(7):993-1000. doi:10.1016/s0002-8223(02) 90228-2.
Byrne CS, Chambers ES, Morrison DJ, Frost G. The role of short chain fatty acids in appetite regulation and energy homeostasis. Int J Obes (Lond). 2015;39(9):1331-1338. doi:10.1038/ijo.2015.84.
Maskarinec G, Takata Y, Pagano I, et al. Trends and dietary determinants of overweight and obesity in a multiethnic population. Obesity (Silver Spring). 2006; 14(4):717-726. doi:10.1038/oby.2006.82.
Flint A, Raben A, Blundell JE, Astrup A. Reproducibility, power and validity of visual analogue scales in assessment of appetite sensations in single test meal studies. Int J Obes Relat Metab Disord. 2000;24(1):38-48. doi:10.1038/sj.ijo.0801083.
Chandra JR, Dasegowda SM et al., Effect of fenugreek fiber flakes on appetite scores and glucose homeostasis in healthy subjects. International Journal of Medical and Health Research. vol. 4; Issue 10; Oct. 2018; p. 14-21.
Mekhri S, Ambarish C et al. Effect of two doses of Fenugreek Flakes (FenuLean TM) on appetite, body-weight and blood glucose homeostasis: A randomized, double-blind, multicenter, three-arm, long-term, control study in 100 healthy subjects. International Journal of Medical Science and Clinical Research vol. 1; Issue 4; Oct. 2019 p. 07-14.

* cited by examiner

*Primary Examiner* — Russell G Fiebig
(74) *Attorney, Agent, or Firm* — MAINLINE INTELLECTUAL PROPERTY

(57) ABSTRACT

The present invention relates to an organoleptically improved dietary fiber composition comprising *Trigonella foenum-graecum* (fenugreek) seeds in the form of flakes with improved palatability, and method(s) of preparing the said composition. More particularly, invention relates to nutrient rich de-bitterised and de-fatted fenugreek dietary fiber and administering the same in a subject to bring satiety, feeling of fullness, appetite suppression, less desire to consume food, which may further lead to reduction or management of weight. The present invention can be used for the development of functional food, dietary plan and as a nutritional supplement. The present invention also relates to methods of managing various conditions such as, but not limited to, management of weight, appetite scores, glucose homeostasis, body mass index and serum insulin levels or any combinations thereof using the said composition.

8 Claims, 9 Drawing Sheets

ORGANOLEPTIC DIETARY PRODUCT FROM FENUGREEK SEED, AND METHOD FOR PRODUCTION THEREOF

PRIORITY PARAGRAPH

This application claims priority to the Indian provisional patent application No. 201941005185, filed on Feb. 9, 2019, titled "ORGANOLEPTIC DIETARY PRODUCT FROM FENUGREEK SEED, AND METHOD FOR PRODUCTION THEREOF" and is incorporated herein by reference.

TECHNICAL FIELD OF THE INVENTION

This invention belongs to the field of an organoleptically improved dietary fiber composition comprising de-bitterised and de-fatted *Trigonella foenum-graecum* (fenugreek) seeds, in the form of flakes with improved palatability, and method(s) of preparing the said composition. Furthermore, the fenugreek flakes are administered in a subject to bring satiety, feeling of fullness, and appetite suppression on consumption.

BACKGROUND OF THE INVENTION

Fenugreek (*Trigonella foenum-gracium*) is an annual leguminous herb possessing wonderful medicinal values. The dried seeds are aromatic and bitter, which have been used traditionally in India, China, Egypt and in some parts of Europe for its well-known medical and rejuvenating effects. The major constituents of fenugreek seeds have been identified as proteins (20-25%), dietary fiber (40-45%), mucilaginous soluble finer (20-25%), fixed fatty acids and essential oils (6-8%) and steroidal saponins (2-5%).

High fiber foods have bulking and viscosity properties which are predominantly responsible for influencing satiation and satiety. Fiber rich foods usually are accompanied by increased efforts and/or time of mastication, which leads to increased satiety through a reduction in rate of ingestion [1].

The effects of dietary fiber on hunger, satiety, and energy intake and body weight has been extensively studied. Several types of fibers increase satiety by increasing stomach distension which can slow gastric emptying. Another possible mechanism by which fibers increase satiety is through fermentation in the gut by microflora and the subsequent effects of short-chain fatty acids (SCFA) produced. SCFA interact with G-coupled protein receptors such as GPR41 and GPR43 on enteroendocrine cells and may be part of the mechanism for the effect of fiber on appetite as they increase production of satiety-related hormones from the colon. All in all, it has shown to reduce energy density, slowed gastric emptying, altered postprandial glycaemic response and the production and secretion of satiety hormones [2].

Ayurvedic literature refers to the usefulness of many plant extracts in the treatment of diabetes mellitus. Fenugreek is used to treat diabetes, migraines, allergies and elevated cholesterol in traditional medicinal practices in India. As per the ancient Indian practice of Ayurveda and Naturopathy, fenugreek seed is traditionally taken in a powdered form, or boiled with water, or as a sprouted seed for the control of blood sugar. Fenugreek in India is used as a culinary spice and also as a medicinal herb. Fenugreek seeds contain about 50% dietary fiber if used as a defatted powder. Similar to Guar Gum, fibers present in the seeds may slow gastric transit time.

Fenugreek or *Trigonella* (botanically) has many other medicinal properties apart from controlling of blood sugar such as anti-catarrhal, anti-Inflammatory, antiseptic, aphrodisiac, astringent, expectorant and fever controlling.

Fenugreek has about 28 percent mucilage 5 percent of a stronger-smelling, bitter fixed oil (which can be extracted by ether) 22 percent proteins, two alkaloids Trigonelline and Choline, a volatile oil, and a yellow coloring substance. It is also rich in complex starch. It is rich in other nutrients such as Iron, Lecithin, Minerals, Biotin, inositol, mucilage, volatile oils, PABA, phosphates, trimethylamine, and vitamins such as A, B1, B2, B3, B5, B6, B9, B12, and D.

It contains saponins, coumarin, fenugreekine, nicotinic acid, phytic acid, scopoletin and trigonelline, all of which are known to lower blood sugar. The aromatic oil of fenugreek is rich in iron, vitamins A and D (similar in composition to cod liver oil).

Apart from these nutrients' fenugreek or trigonella is a rich source of dietary fiber. Both soluble and insoluble forms fiber are present to the extent of 50-60% which makes it a good source of natural fiber. But the bitterness poses a problem. Once the bitterness is removed and de-fatted the fenugreek becomes a best alternative for dietary fiber that can be consumed on a daily basis. Fiber becomes a necessary part of nutrition since it helps in cleansing the intestines, removes toxins, and facilitates good bowel movement. If the same fiber comes from a natural source like fenugreek that is rich in proteins, good starch, vitamins and minerals, it is an added advantage and the fenugreek fiber not only cleanses the body but also controls sugar metabolism and can further help in maintaining optimal body weight. Therefore, the de-bitterised and de-fatted fiber from fenugreek can be a good choice for weight reduction coupled with nutrition. In this connection many reports of documented literature available with regard to extraction of active ingredients from fenugreek, dietary fiber from fenugreek, formulations using fenugreek proteins, use of fenugreek fiber as binding agent, also as food additive [3].

PRIOR ART DOCUMENTS

U.S. Pat. No. 5,658,571A disclosed a process for preparing de-bitterised powder of the seed of the plant fenugreek (*Trigonella Foenum-graecum*). The de-bitterised powder of the seed and formulations containing the de-bitterised powder of the seed of fenugreek are useful as fiber supplements. Guar gum and bran can be blended with the de-bitterised powder of the seed of Fenugreek to prepare formulations which can be used as fiber supplements. Steam treatment is given to the seeds along with the solvent treatment.

U.S. Pat. No. 6,495,175B2 disclosed a method for obtaining substantially pure fixed oil(s), oleoresin and dietary fiber from fenugreek seeds. The method employs two different solvent extraction stages, wherein the first extraction isolates fixed oils and the second extraction isolates oleoresin. The dietary fiber remaining after extraction is clean, approximately light yellow to light brown, substantially tasteless and substantially odorless. An extraction system for conducting the extractions is also provided. The extraction system includes a condenser, a seed holding extraction vessel, a reboiler, solvent and extract reservoir and a feedback loop. The extraction solvent is obtained from the reboiler and it is contacted with the fenugreek seeds after condensation in the condenser. The extraction system employs minimal amounts of solvent compared to conventional processes. In terms of color, taste, and/or odor, the food grade isolated fixed oils, oleoresin and dietary fiber are superior to those products obtained from conventional extraction processes. This invention employed hexane, iso-propanol and ethanol.

US20130071470A1 disclosed a method of lowering blood cholesterol in a non-diabetic patient by at least 30%. The method involves orally administering for 30 consecutive days a fenugreek seed extract composition. Various methods of preparation and various formulations are described. Physiologically effective pharmaceutical compositions and beverages containing fenugreek seed extracts and other active components are also disclosed. Here, there is no mention about the dietary fiber from fenugreek.

Patent No. WO2017046777 disclosed a composition comprising Trigofoenoside, Vitexin, Iso-vitexin, Vitexin-2-o-rhamnoside Vicenin-1 and fiber, optionally along with pharmaceutically acceptable excipient(s) and method(s) of preparing said composition. The present disclosure also relates to methods of managing various conditions such as, but not limited to, Hypoxia, Pulmonary Hypertension, Pulmonary Fibrosis and Sinusitis using the said composition. Fenugreek seeds are subjected to flaking to obtain flakes of size 2 mm in a flaker and subjected series of extractions with many solvents including ethyl acetate but nothing is mentioned about the dietary fiber and subsequent usage of the same for consumption in the form of flakes before meal.

Patent No. 20100247638A1 disclosed an organoleptically improved dietary fiber composition from *Trigonella foenum-graecum*. In addition, the present invention provides a process to obtain an organoleptically improved dietary fiber composition comprising protein and galactomannans. This invention uses powdered fenugreek seeds and subjects the powder to solvent extraction obtain dietary fiber in the form of yellow powder but not in the form of flakes.

Patent No. 20040228932A1 disclosed a novel solvent free process of obtaining an insoluble fiber rich fraction from *Trigonella foenum-graceum* seeds. The multifunctional fiber rich fraction (FRF) and highly purified FRF are useful as excipients for pharmaceutical dosage forms for various routes of administration. These excipients can be used as binder, disintegrant, filler, dispersing agent, coating agent, film forming agent, thickener and the like, for preparation of variety of dosage forms. FRF and highly purified FRF can also be used in a controlled release, targeted release and other specialized delivery systems, as well as in food and uses series powdering and sieving steps.

U.S. Pat. No. 5,997,877A disclosed a process for the fractionation of fenugreek seeds (*Trigonella foenum-graecum*) and extraction of the various fractions thereof. The process has a high yield rate, and provides a number of high-quality fractions of the fenugreek seed including a soluble dietary fiber fraction, de-flavored fenugreek seed, high-protein fenugreek meal, and dioscin and other saponins, along with the fenugreek oleoresins which have conventional commercial use. Nothing is disclosed about the fenugreek flakes.

Patent No. WO/1999/025197 disclosed fenugreek seed material having reduced odor and taste. Products derived from the fenugreek seed material are also provided. The fenugreek seed material of the invention has reduced odor and taste compared to native fenugreek but maintains all of the biological activity of native fenugreek. Methods for reducing the intestinal absorption of a caloric and/or cholesterol compound from a caloric and/or cholesterol containing comestible in a human and for removing cholesterol from a cholesterol containing comestible are also provided. Here fenugreek seeds are powdered subjected to series of solvent extractions and finally a powder is obtained.

However, none of the prior arts discloses an easy way of administering the fenugreek dietary fiber in the form of flakes as a method of weight management and producing de-bitterised and de-fatted fenugreek flakes in an efficient and effective way that can consumed by any person above the age of 5 years except pregnant women on a daily basis before meal.

So, there is a need to develop organoleptically dietary fiber composition from *Trigonella foenum-graecum* seeds in the form of flakes with improved palatability for management of weight, appetite scores, glucose homeostasis, Body Mass Index and serum insulin levels or any combinations thereof.

In summary, there is a need in the art to develop a fenugreek dietary fiber in the form of de-bitterised and de-fatted fenugreek flakes that can easily consumed by any person.

Hence, the present invention overcomes the various drawbacks observed in prior arts and provides methods for arriving at composition comprising de-bitterised and de-fatted *Trigonella foenum-graecum* flakes with improved palatability. The composition of the present invention is effective in managing conditions such as, but not limited to, management of weight, appetite scores, glucose homeostasis, Body Mass Index and serum insulin levels.

SUMMARY AND OBJECTS OF THE INVENTION

The primary objective of the present invention is to provide a method of producing de-bitterised, de-fatted *Trigonella foenum-graecum* (fenugreek) dietary fiber in the form of flakes with improved palatability, optionally along with acceptable additives and method(s) of preparing the said composition.

In one embodiment, an organoleptically improved the fenugreek flake composition is administered in a subject to bring satiety, feeling of fullness, and appetite suppression on consumption.

In another embodiment, the *Trigonella foenum-graecum* flakes along with acceptable additives have concentration of protein ranging from about 15% w/w to about 40% w/w, and the fiber is present at concentration ranging from about 25% w/w to about 65% w/w, wherein the soluble fiber comprising galactomannans is present at concentration ranging from about 10% w/w to about 26% w/w and insoluble fiber is present at concentration ranging from about 15% w/w to about 39% w/w.

In another embodiment, the *Trigonella foenum-graecum* flakes comprises amino acids, L-Arginine—0.1% to 3%, L-Tryptophan—0.1% to 2%, L-Leucine—0.1% to 2%, and L-Isoleucine—0.1% to 1.5%.

According to exemplary aspects, the present invention relates to a method for obtaining composition comprising organoleptically dietary fiber *Trigonella foenum-graecum*, in the form of flakes with improved palatability, optionally along with acceptable additives, wherein the said method comprising acts of:

cleaning & sorting of *Trigonella foenum-graecum* seeds to remove any damaged and discolored seeds;
soaking the sorted seeds;
pulverizing to obtain the required particle size;
extracting the pulverized seeds with a mixture of first solvent and external heat;
treating the first extract with a second solvent and external heat to obtain second extract;

re-extracting the second extract with a third solvent and external heat to obtain a clear extract;

filtering the extract to remove the fenugreek soft extract comprising saponins and the fixed oil;

separating the extracted components; wherein the extracted components are de-bitterised and de-fatted fenugreek flakes (FenuLean®);

drying the de-bitterised and de-fatted fenugreek flakes (FenuLean®) to remove the solvent;

analysing & packing of de-bitterised and de-fatted fenugreek flakes (FenuLean®), optionally adding acceptable additives.

Also disclosed herein, extraction with solvents are carried out at temperature ranging from about 60° C. to about 90° C., preferably about 65° C. to about 75° C., for time period of about 3 hours to about 8 hours, preferably about 5 hours; and wherein said solvents are aliphatic compounds selected from group comprising methanol, ethanol, anhydrous ethanol, propanol, butanol, ethyl acetate or combinations thereof, wherein the preferable solvent is ethanol.

In an additional embodiment, the extraction is continued on an interval of 3-8 hours in which the saponins and the fixed oil fractions are reduced to a level of no more than 0.5%.

In a further embodiment, the de-bitterised and de-fatted fenugreek flakes are substantially less bitter than otherwise identical raw fenugreek seeds, wherein the de-bitterised and de-fatted fenugreek flakes are used in food products.

In additional embodiments, a food product comprising the de-bitterised and de-fatted fenugreek flakes are selected from the group comprising of cookies, cereals, crackers, pizza dough, juices, gravies, salads, breads, pastries, breakfast cereals, cakes, other baked goods, tortillas, powdered drink mixes, other beverages, sauces, doughnuts, bagels, biscuits, pasta, gummies, candies or any combinations thereof.

According to exemplary aspects, the present invention relates to a method of managing a condition in a subject; wherein the said condition comprising management of weight, appetite scores, glucose homeostasis, Body Mass Index and serum insulin levels or any combinations thereof; wherein the said method comprising act of administering composition comprising *Trigonella foenum-graecum* flakes along with acceptable additives to the subject in need thereof.

In additional embodiment, a method of managing a condition in a subject, wherein the de-bitterised and de-fatted fenugreek flake composition is administered at dose ranging from about 5 g to about 10 g per day.

According to yet another exemplary aspects, the present invention relates to a method of managing a condition in a subject, wherein the de-bitterised and de-fatted fenugreek flakes are safe, non-toxic, gluten-free and free of adverse effects.

In further embodiment, a method of managing a condition in a subject, wherein the subject observes satiety, feeling of fullness, appetite suppression, less desire to consume food, wherein the de-bitterised and de-fatted fenugreek flakes control the food intake in normal individuals who want to use diet as a method to control energy intake.

Furthermore, the invention also provides methods,

To obtain de-bitterised and de-fatted dietary fiber from *Trigonella* (Fenugreek) in the form of flakes.

To administer the fenugreek flakes to the subject before meal to evaluate the efficiency in hunger suppression and in creating satiety feeling in the subject.

To perform clinical studies by administering the dietary fiber from fenugreek in the form of flakes (fibers) to the subjects belonging to various groups to come out with the effective portion size that can be safely administered for achieving the targeted goal of weight reduction.

According to a non-limiting exemplary aspect of the present invention, fenugreek flakes 5 g and 10 g showed an acceptable safety profile and a positive efficacy trend in improving the satiety in healthy adult subjects. 10 g dose of fenugreek flakes added to a meal increased satiety and fullness and decreased hunger and prospective need of food in VAS scores.

According to further non-limiting exemplary aspect of the present invention, the total palatability scores were found to be better with fenugreek flakes 10 g than 5 g. Though the study was a comparison of fenugreek flakes of 5 g versus 10 g, compared to baseline there was a significant change in reported scores of satiety, fullness, hunger, desire to consume food and prospective need of food amongst subjects on fenugreek flakes of 5 g and 10 g. Study results suggest that fenugreek flake has a role in the control of food intake in normal individuals who want to use diet as a method to control energy intake through their effects on appetite suppression and in food intake.

Several aspects of the invention are described below with reference to examples for illustration. However, one skilled in the relevant art will recognize that the invention can be practiced without one or more of the specific details or with other methods, components, materials and so forth. In other instances, well-known structures, materials, or operations are not shown in detail to avoid obscuring the features of the invention. Furthermore, the features/aspects described can be practiced in various combinations, though only some of the combinations are described herein for conciseness.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings.

In the drawings, like reference numbers generally indicate identical, functionally similar, and/or structurally similar elements. The drawing in which an element first appears is indicated by the leftmost digit(s) in the corresponding reference number.

DETAILED DESCRIPTION OF THE INVENTION

Figure 1:
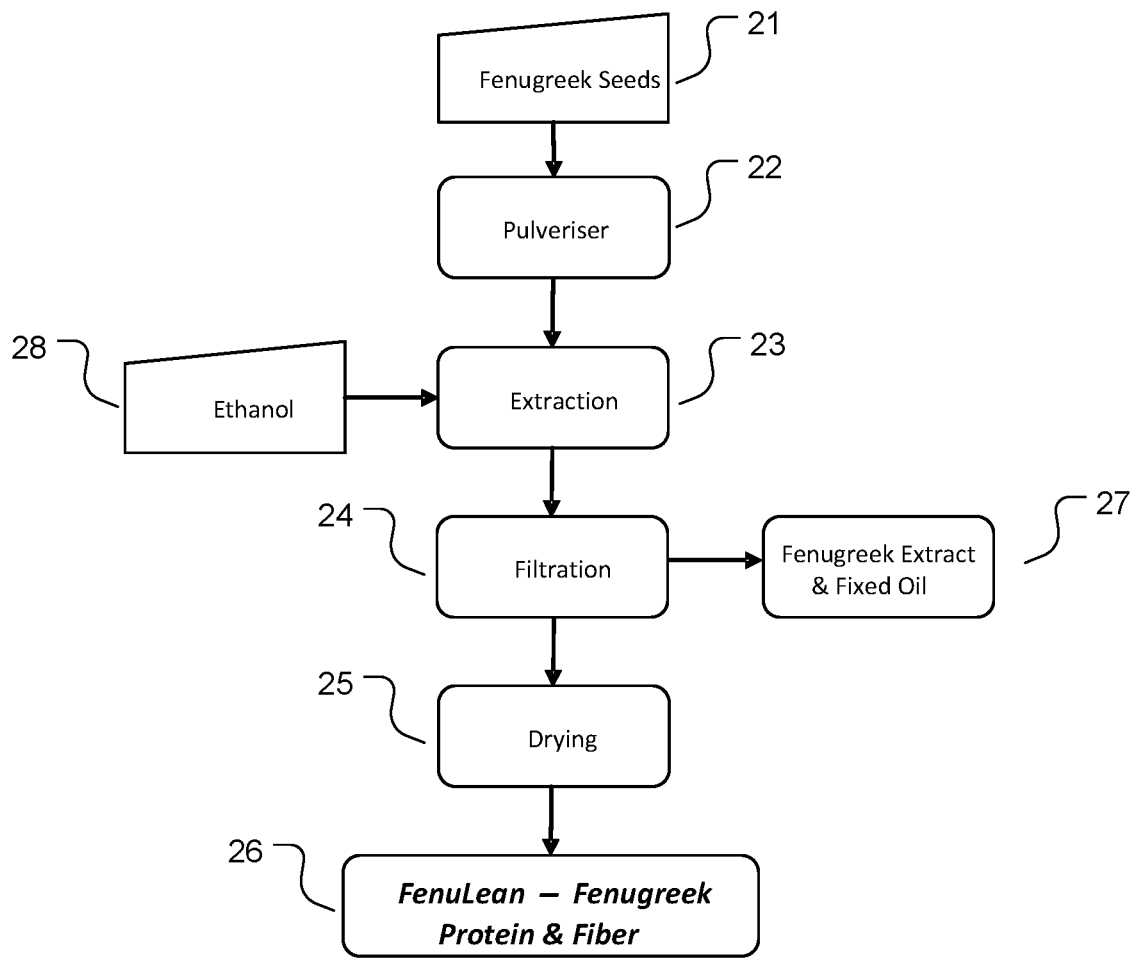
FIG. 1 is a process flow diagram illustrating one presently preferred embodiment for obtaining composition comprising organoleptically dietary fiber *Trigonella foenum-graecum*, in the form of flakes with improved palatability, optionally along with acceptable additives, according to the aspects of present invention.

It is to be understood that the present invention is not limited in its application to the details of construction and the arrangement of components set forth in the following description or illustrated in the drawings. The present invention is capable of other embodiments and of being practiced or of being carried out in various ways. Also, it is to be understood that the phraseology and terminology used herein is for the purpose of description and should not be regarded as limiting.

The use of "including", "comprising" or "having" and variations thereof herein is meant to encompass the items listed thereafter and equivalents thereof as well as additional items. The terms "a" and "an" herein do not denote a limitation of quantity, but rather denote the presence of at least one of the referenced items. Further, the use of terms "first", "second", and "third", and the like, herein do not denote any order, quantity, or importance, but rather are used to distinguish one element from another.

As used herein, the singular forms "a", "an", and "the" include both singular and plural referents unless the context clearly dictates otherwise. By way of example, "a dosage" refers to one or more than one dosage.

The terms "comprising", "comprises" and "comprised of" as used herein are synonymous with "including", "includes" or "containing", "contains", and are inclusive or open-ended and do not exclude additional, non-recited members, elements or method steps.

The terms "Solvent Storage tanks" means tank for storing solvents.

The terms "Extractor" means an equipment for processing the raw material.

The term "managing" or "management" includes preventing, treating and healing of a condition or disorder or ill effects or side effects. The term also encompasses maintenance of the optimum state and prevention of the further progress in the condition or disorder or ill effects or side effects.

The term "subject" is an animal or a mammal, including human beings.

All documents cited in the present specification are hereby incorporated by reference in their totality. In particular, the teachings of all documents herein specifically referred to are incorporated by reference.

Example embodiments of the present invention are described with reference to the accompanying figures.

In the drawings, like reference numbers generally indicate identical, functionally similar, and/or structurally similar elements. The drawing in which an element first appears is indicated by the leftmost digit(s) in the corresponding reference number.

EMBODIMENTS OF THE INVENTION

FenuLean® is a proprietary product of company BIO-GEN EXTRACTS PRIVATE LIMITED.

In an embodiment, invention deals with an organoleptically dietary fiber composition comprising *Trigonella foenum-graecum*, in the form of flakes with improved palatability, optionally along with acceptable additives.

In an alternative embodiment, the acceptable additive is selected from group comprising gum, granulating agents, binding agents, lubricating agents, disintegrating agents, sweetening agents, coloring agents, flavoring agents, coating agents, plasticizers, preservatives, suspending agents, emulsifying agents, sweetening agents, antioxidants, surfactants, viscosity enhancers, plant cellulosic materials, additives, solvents, glidants, anti-adherents, anti-static agents, preservatives, suspending agents and spheronization agents or any combinations thereof.

In an additional embodiment, the composition *Trigonella foenum-graecum* flakes along with acceptable additives have concentration of protein ranging from about 15% w/w to about 40% w/w, and the fiber is present at concentration ranging from about 25% w/w to about 65% w/w, wherein the soluble fiber comprising galactomannans is present at concentration ranging from about 10% w/w to about 26% w/w and insoluble fiber is present at concentration ranging from about 15% w/w to about 39% w/w.

In another embodiment, the *Trigonella foenum-graecum* flakes comprises amino acids, L-Arginine—0.1% to 3%, L-Tryptophan—0.1% to 2%, L-Leucine—0.1% to 2%, and L-Isoleucine—0.1% to 1.5%.

In further embodiment, the shelf-life of the composition is about 2 years from the date of manufacture that are packed in air tight containers with inner LDPE (Low-density polyethylene) packing with outer HDPE (High-density polyethylene) drum material.

In an exemplary embodiment, a method for obtaining composition comprising organoleptically dietary fiber *Trigonella foenum-graecum*, in the form of flakes with improved palatability, optionally along with acceptable additives, wherein the said method comprising acts of:
cleaning & sorting of *Trigonella foenum-graecum* seeds to remove any damaged and discoloured seeds;
soaking the sorted seeds;
pulverizing to obtain the required particle size;
extracting the pulverized seeds with a mixture of first solvent and external heat;
treating the first extract with a second solvent and external heat to obtain second extract;
re-extracting the second extract with a third solvent and external heat to obtain a clear extract;
filtering the extract to remove the fenugreek soft extract comprising saponins and the fixed oil;
separating the extracted components; wherein the extracted components are de-bitterised and de-fatted fenugreek flakes (FenuLean®);
drying the de-bitterised and de-fatted fenugreek flakes (FenuLean®) to remove the solvent;
analysing & packing of de-bitterised and de-fatted fenugreek flakes (FenuLean®), optionally adding acceptable additives.

In further embodiment, the extraction with the solvents are carried out at temperature ranging from about 60° C. to about 90° C., preferably about 65° C. to about 75° C., for time period of about 3 hours to about 8 hours, preferably about 5 hours; and wherein said solvents are aliphatic compounds selected from group comprising methanol, ethanol, anhydrous ethanol, propanol, butanol, ethyl acetate or combinations thereof, wherein the preferable solvent is ethanol.

In an additional embodiment, the act of extractions may be repeated 3-6 times, wherein said solvents are a mixture of aliphatic alcohol and deionized water; and wherein the preferable ratio of aliphatic alcohol to deionized water is about 80:20.

In an embodiment, the extraction is continued on an interval of 3-8 hours in which the saponins and the fixed oil fractions are reduced to a level of no more than 0.5%.

In an additional embodiment, the drying is carried out in a solar tent or vacuum tray drier, and under controlled temperature and humidity.

In a further embodiment, the first solvent, the second and the third solvent are independently selected from a group comprising water, aliphatic alcohol and/or combinations thereof. In addition the extraction is carried out for a time period ranging from about 3 hours to about 15 hours. The extracted components are separated by method comprising filtration, centrifugation, sedimentation and/or combinations thereof.

In an exemplary embodiment, the de-bitterised and de-fatted fenugreek flakes are substantially less bitter than otherwise identical raw fenugreek seeds, wherein the de-bitterised and de-fatted fenugreek flakes are used in food products. In addition, the food products are selected from the group comprising of cookies, cereals, crackers, pizza dough, juices, gravies, salads, breads, pastries, breakfast cereals, cakes, other baked goods, tortillas, powdered drink mixes, other beverages, sauces, doughnuts, bagels, biscuits, pasta, baked goods, candies or any combinations thereof. The flakes can also be mixed with other food products like roti, chapatti, and pakoras to enhance their overall nutrition value.

In a further embodiment, a method of managing a condition in a subject; wherein the said condition comprising management of weight, appetite scores, glucose homeostasis, Body Mass Index and serum insulin levels or any combinations thereof; wherein the said method comprising act of administering composition comprising *Trigonella foenum-graecum* flakes along with acceptable additives to the subject in need thereof. The subject is an animal or human being.

The method of managing a condition in a subject and the said method comprising administering an effective and acceptable amount of organoleptically improved dietary fiber composition obtained from *Trigonella foenum-graecum*, optionally along with acceptable additives to the subject. Furthermore, the composition is administered at dose ranging from about 5 g to about 10 g per day.

In a further embodiment, the de-bitterised and de-fatted fenugreek flakes are safe, non-toxic, gluten-free and free of adverse effects. In addition, administering an effective and acceptable amount of organoleptically improved dietary fiber composition, the subject observes satiety, feeling of fullness, appetite suppression, less desire to consume food, wherein the de-bitterised and de-fatted fenugreek flakes control the food intake in normal individuals who want to use diet as a method to control energy intake.

In an additional embodiment, the particle size of the de-bitterised and de-fatted fenugreek flakes are between 0.4 mm to 6 mm, with a preferable size of 3 mm to 5 mm, with not more than 25% Passing through 30 mesh and not more than 10% Passing through 40 mesh.

DETAILED PROCESS OF THE INVENTION

Equipment Used

Pulverizer.
Solvent storage tanks.
External jacket for heating.
Distiller.
Vacuum Dryer.
Packing in internationally accepted packing solution.

Raw Materials

Fenugreek seeds.
Aliphatic Alcohol
Water

Process

The fenugreek seeds are received at the warehouse and then sorted to remove any damage & discoloured seeds.

Method of Obtaining Flakes

The invention further discloses the method of producing fenugreek fiber flakes (FIG. 1) comprising acts of:
cleaning & sorting of *Trigonella foenum-graecum* seeds to remove any damaged and discoloured seeds; 21
soaking the sorted seeds;
pulverizing to obtain the required particle size; 22
extracting the pulverized seeds with a mixture of first solvent and external heat; 23 and 28 treating the first extract with a second solvent and external heat to obtain second extract; 23 re-extracting the second extract with a third solvent and external heat to obtain a clear extract; 23 filtering the extract to remove the fenugreek soft extract comprising saponins and the fixed oil; 24 and 27 separating the extracted components; wherein the extracted components are de-bitterised and de-fatted fenugreek flakes (FenuLean®); 24 drying the de-bitterised and de-fatted fenugreek flakes (FenuLean®) to remove the solvent; 25 analysing & packing of de-bitterised and de-fatted fenugreek flakes (FenuLean®), optionally adding acceptable additives 26.

FIG. 1 shows is a process flow diagram illustrating one presently preferred embodiment for obtaining composition comprising organoleptically dietary fiber *Trigonella foenum-graecum*, in the form of flakes with improved palatability, optionally along with acceptable additives, according to the aspect of present invention.

Fenugreek seeds are taken, cleaned thoroughly and sorted out. The sorted seeds are then soaked for a few hours. The sorted fenugreek seeds are weighed for the required batch size to be manufactured. The seeds are then sent to the pulverizer and are reduced to the required particle size. These pulverized or flaked seeds are weighed again and loaded into the extractor (weighing is done again as there is loss of moisture during the process).

The pulverized seeds are subjected to extraction using a mixture of aliphatic compound and deionized water in ratio of about 80:20. The aliphatic compounds selected from group comprising methanol, ethanol, anhydrous ethanol, propanol, butanol, ethyl acetate or combinations thereof. The solvent from the Solvent Storage tanks is pumped into the extractor in appropriate ratio of aliphatic compound and deionized water (ratio 1:3). External heat is applied to assist in better extraction. The process of extraction and re-extraction is continued on an interval of 3-8 hours in which the saponins and the fixed oil fractions are reduced to a level of no more than 0.5%.

After the process of extraction and re-extraction, the extracted components are de-bitterised and de-fatted fenugreek flakes (FenuLean®); 24 and are further dried to remove the solvent; 25

Upon completion of the extraction, the material is unloaded to produce:

The fenugreek extract,

The fixed oil, and

The de-bitterised and de-fatted fenugreek flakes (FenuLean).

The de-bitterised and de-fatted fenugreek flakes are taken to a solar tent or vacuum tray drier and under controlled temperature and humidity are completely dried so that there is no solvent present in the final product or reduced to a level of no more than 0.5%.

The product is obtained in the form of suitable flakes by regulation of temperature and quantity of the solvent used for extraction. The final product with a shelf-life of 2 years from the date of manufacture are packed in air tight containers with inner LDPE (Low-density polyethylene) packing with outer HDPE (High-density polyethylene) drum material. The product is devoid of preservatives, colorants and enhancers. The invention further discloses the clinical studies on various groups, both sexes, ages above 5 years, 30 minutes before the meal to evaluate postprandial glucose control, obesity control, hunger suppression (satiety).

Figure 2:
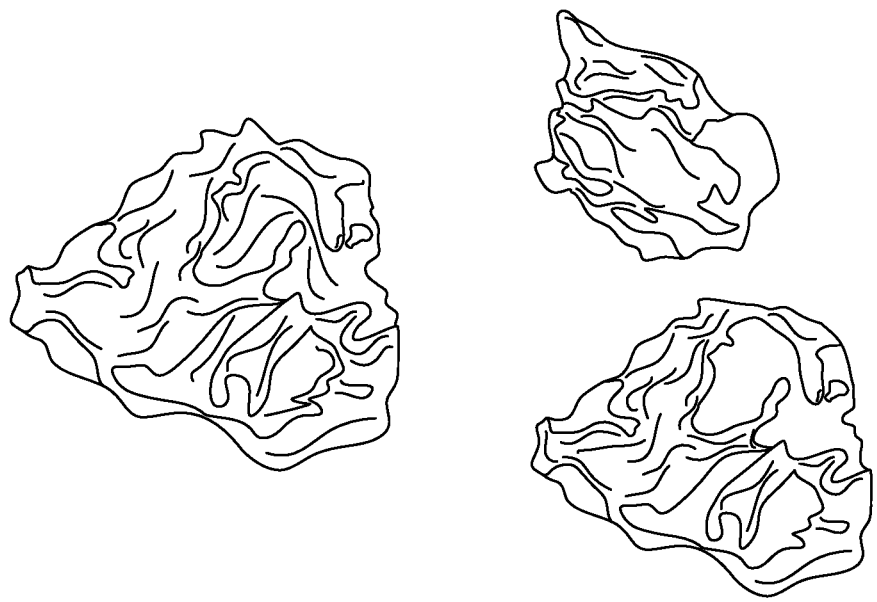
FIG. 2 depicts illustrative schematic diagram of fenugreek flakes, according to the aspects of present invention.

The particle size of the product is between 0.4 mm to 6 mm, with a preferable size of 3 mm to 5 mm, with not more than 25% passing through 30 mesh and not more than 10% passing through 40 mesh. FIG. 2 depicts illustrative schematic diagram of fenugreek flakes, according to the aspect of present invention.

The invention further describes the benefits of the consumption of 5-0 gms fenugreek flakes as an excellent option since it provides the nutrition devoid of bitterness, and fat in the form of flakes that are chewable, do not stick to the palate unlike the dietary fiber powders, provides good nutrition since it contains resistant starch. The *Trigonella foenum-graecum* flakes along with acceptable additives have concentration of protein ranging from about 15% w/w to about 40% w/w, and the fiber is present at concentration ranging from about 25% w/w to about 65% w/w, wherein the mucilaginous soluble fiber comprising galactomannans in which galactose to mannose ratio is 1:1, which contributes to the more hydrolyzability and solubility is present at concentration ranging from about 10% w/w to about 26% w/w and insoluble fiber is present at concentration ranging from about 15% w/w to about 39% w/w.

In an alternative embodiment of the present invention, the composition may be obtained by chemical synthesis.

In an exemplary embodiment, the composition of the present invention is used to manage a condition in a subject such as condition comprising management of weight, appetite scores, glucose homeostasis, Body Mass Index and serum insulin levels or any combinations thereof; wherein the said method comprising act of administering composition comprising *Trigonella foenum-graecum* flakes along with acceptable additives to the subject in need thereof. In addition, the method of administering the said composition can be used for obesity control, and diabetes control in the long run.

In a non-limiting embodiment of present invention, administration of the composition is carried out orally.

In still another embodiment of the present invention, the instant composition is formulated into a suitable dosage formulation for obtaining a therapeutic effect.

The method of managing a condition in a subject, wherein the de-bitterised and de-fatted fenugreek flake composition is administered at dose ranging from about 5 g to about 10 g per day. The de-bitterised and de-fatted fenugreek flakes are safe, non-toxic, gluten-free and free of adverse effects. Administering of the same in suitable amounts before breakfast or meals so that the subject gets a feeling of satiety and fullness which may further lead to weight management. The method of managing a condition in a subj ect, wherein the subject observes satiety, feeling of fullness, appetite suppression, less desire to consume food, wherein the de-bitterised and de-fatted fenugreek flakes control the food intake in normal individuals who want to use diet as a method to control energy intake.

The present invention is further elaborated with the help of the following examples. However, these examples should not be construed to limit the scope of the present invention.

Example 1

Effect of Fenugreek Flakes (FenuLean®) on Appetite Scores and Glucose Homeostasis in Healthy Subjects [5]

It is hypothesized that high fiber foods displace energy as they have much lower energy density compared with high fat food. The bulking and viscosity properties of dietary fiber are predominantly responsible for influencing satiation and satiety. The main objective was to determine efficacy and safety.

Methods

Study group consisted of eighteen healthy subjects between age group of 18 and 65 years of age. The study was carried out at Rajalakshmi hospital and was approved by Rajalakshmi hospital institutional review board. It was confirmed that ethics committee of Rajalakshmi hospital is constituted and functions as per Good Clinical Practice guidelines.

Selection of Subjects

Men and women aged 18 to 65 years with body mass index (BMI)≤25 kg/m2 with no other metabolic disorders and those who were willing to give informed consent were included in the study. Subjects with hypertension and diabetes and other unstable medical conditions were excluded from the study. Women who were pregnant, breast feeding and planning pregnancy were excluded from the study.

Statistical Analysis

Data analyses were performed using the following software: SAS® for Windows 95/NT (Version 9.1 or higher, SAS Institute, Cary, N.C., USA). Area under the curve (AUC) was calculated using trapezoidal rule using WinNonlin® software (Version 5.3). ANCOVA (Analysis of covariance) was performed for the primary variables using baseline as covariates else paired or independent t-test were performed between the treatments. AUC of the VAS satiety scores was calculated using trapezoidal rule. The baseline characteristics were compared among treatment groups. The baseline characteristics which were found to be significant between study groups were accounted in primary analysis model. For continuous variables (age etc.), data was summarized using number of subjects (N), mean, standard deviation (SD), median, minimum and maximum. For categorical variables, data was presented with the number of exposed subjects, number with percentage in various categories of the endpoint, where percentage was based on the exposed subjects. The descriptive variables (gender etc.) were evaluated using Cochran-Mantel-Haenszel test stratified by study center at 0.05 level of significance.

Study Design

Subjects were randomly assigned into two groups (test arm 1 and test arm 2) using blocked randomization method in SAS (version 9.1).

Eighteen healthy, normal weight (BMI 18 to 24.9) subjects, 18-65 years of age participated in the study. All subjects underwent screening procedures after the informed consent process at Visit 1.

Subjects who passed the eligibility criteria were randomized into two treatment arms to receive fenugreek flakes either 5 g or 10 g in 1:1 ratio on Visit 2.

Subjects recorded the satiety and palatability ratings on VAS scales [4]. The subjects underwent crossover of the treatment arms in the next visit (Visit 3). The subjects who received fenugreek flakes 5 g received 10 g and vice versa. There was a washout period of three days between the crossover visits.

Questionnaires

VAS, 100 mm in length with words anchored at each end, scoring expressing the most positive and the most negative, were used to assess hunger, satiety, fullness, prospective food consumption, desire to consume food and palatability. The questionnaires were given to subjects and were instructed to do the ratings.

Appetite and palatability scores were measured using VAS questionnaires ratings.

Serum insulin levels were assessed using Elecsys insulin assay (electro-chemiluminescence immunoassay method) at the study centre's local laboratory. Around 5 ml blood was drawn at baseline after overnight fasting and after the meal at time points up to 180 minutes post prandial.

Blood glucose levels were assessed using one touch glucometer (batch no: ZA12702, Expiry date: November 2020) at fasting levels and at intervals of 15, 30, 45, 60, 90, 120, 150 and 180 minutes from the start of meal.

Investigational Product (PI)

Fenugreek flakes are proprietary products of Bio-gen Extracts Pvt. Ltd. The products were defatted and debitterized. The compound is in the form of flakes. The composition of fenugreek flakes is as shown in table I.

TABLE 1

| Parameter | Results |
| --- | --- |
| Protein content | 32.57 g/100 g |
| Total dietary fiber | 49.46 g/100 g |
| Soluble dietary fiber | 18.68 g/100 g |
| Insoluble dietary fiber | 30.78 g/100 g |
| Total fat content | 0.45 g/100 g |
| Iron (Fe) | 18.97 mg/100 g |
| Calcium (Ca) | 1927.54 mg/100 g |
| Potassium (K) | 1321.74 mg/100 g |
| Sodium (Na) | 71.40 mg/100 g |
| Magnesium (Mg) | 164.39 mg/100 g |
| Total Amino acid | 9.05 g/100 g |
| Gluten content | <5 mg/kg |

Appetite and palatability scores were measured using VAS questionnaires ratings.

Primary Efficacy Analysis

Changes from baseline for all the primary endpoints such as blood glucose levels, satiety, fullness, hunger, desire to consume food and prospective food consumption VAS score and insulin response were evaluated to assess the functional benefits of fenugreek flakes. Descriptive statistics were performed. Sub group analysis was performed for 2 groups by treatment and the data will be presented in appropriate charts. ANCOVA (Analysis of covariance) was performed for the primary variables using baseline as covariates else paired or independent t-test were performed between the treatments.

Satiety, fullness, hunger, desire to consume food and prospective food consumption Rating Assessment.

Subjects VAS ratings were converted to a numerical score (0 to 100) from the far-left anchor of the scale. Peak scores (mm) as well as area under curve (AUC, mm*h) was calculated. The cut-off for AUC was 3.5 hours. AUC was calculated using the trapezoidal rule.

For satiety, ratings of 0 on the scales=I am completely empty. Ratings of 100=I cannot eat another bite.

For hunger, ratings of 0=I am not hungry at all. Ratings of 100=I have never been more-hungry.

For fullness, ratings of 0 on the scales=I am not at all full. Ratings of 100=I am totally full.

For desire to consume food, ratings of 0 on the scales=I do have desire to eat. Ratings of 100=I do not have desire to eat food.

For prospective consumption of food, ratings of 0 on the scales=I do like to eat. Ratings of 100=I do not like to eat.

Secondary Efficacy Analysis

Post consumption of the IP the effect of fenugreek flakes on the visual, taste, smell and palatability of test products at each visit was compared by paired t-tests.

Results

All eighteen subjects completed the study (17 male and 1 female). Their mean age±SD was 26.44±12.92 years and their mean BMI was 21.15.

Results of appetite ratings for satiety, hunger, fullness and prospective food consumption are listed in table 2.

TABLE 2

| | Fenugreek Fiber Flakes | | |
|---|---|---|---|
| Measurements [AUC (mm * hr)] | 5 grams (N = 18) | 10 grams (N = 1.8) | p-value [a] |
| Desire to consume food score | 1062.92 ± 164.35 | 735.00 ± 188.60 | 0.0001 |
| Satiety score | 1270.83 ± 252.46 | 1449.16 ± 222.94 | 0.0146 |
| Prospective food consumption score | 993.33 ± 256.28 | 707.08 ± 252.97 | 0.0080 |
| Hunger score | 970.42 ± 168.28 | 687.08 ± 211.63 | 0.0006 |
| Fullness score | 1277.16 ± 230.37 | 1487.50 ± 186.41 | 0.0101 |

Mean ± SD
[a] p-value is from paired t-test.

The subjects underwent fasting and postprandial blood sugar investigations by standardised glucometer and serum insulin tests at various time points as planned in the study.

Example 1.1

Effect of Fenugreek Flakes on Satiety in Healthy Subjects

For satiety, ratings of 0 on the scale=I am completely empty. Ratings of 100=I cannot eat another bite.

Figure 3:
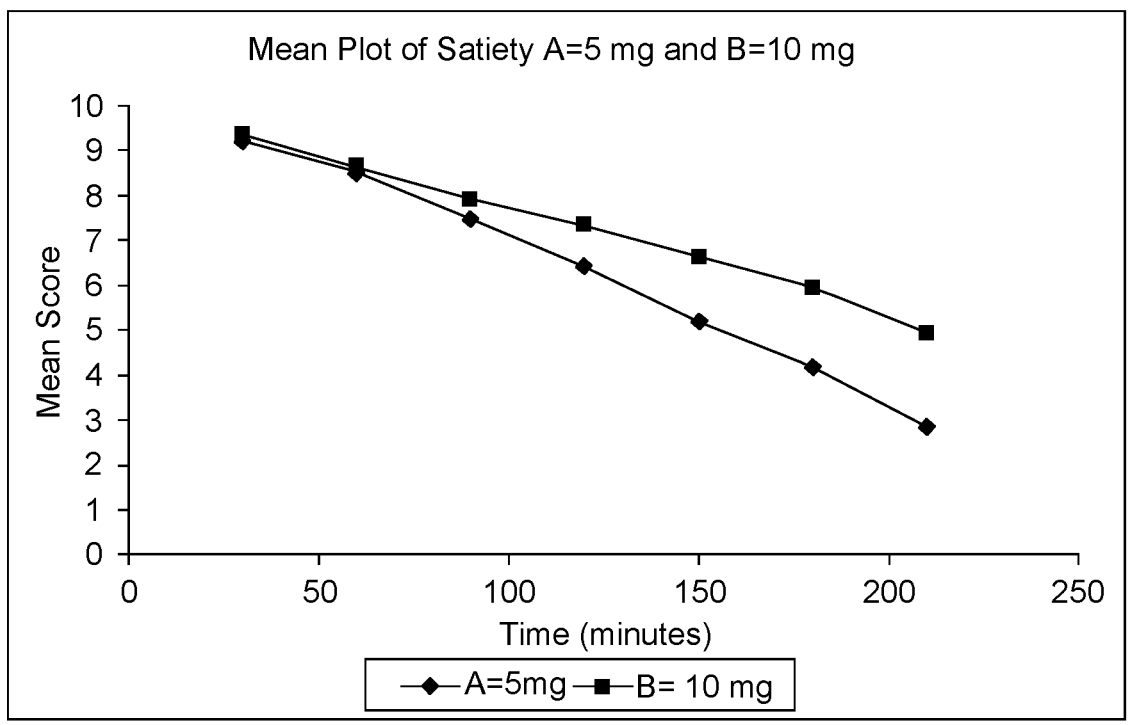
FIG. 3 represents a graph illustrating the Mean plot of satiety scores by treatment A=5 g and B=10 g (N=18). Mean (mm), time (mins), according to the aspects of present invention.

Mean plot of satiety scores by treatment is presented in FIG. 3.

Peak satiety scores were found to be higher with fenugreek flakes 10 g compared to 5 g.

Fenugreek flakes 10 g resulted in a higher AUC (p=0.0146) for satiety scores compared to 5 g.

Satiety scores increased from 30 minutes post consumption of fenugreek flakes 5 g and 10 g compared to before consumption score at baseline and steadily reduced over a period of time in the study.

FIG. 3 represents a graph showing yet another schematic plot illustrating the Mean plot of satiety scores by treatment A=5 g and B=10 g (N=18). Mean (mm), time (mins).

Example 1.2

Effect of Fenugreek Flakes on Hunger Scores in Healthy Subjects

For hunger ratings of 0=I am not hungry at all. Ratings of 100=I have never been more hungry.

Figure 4:
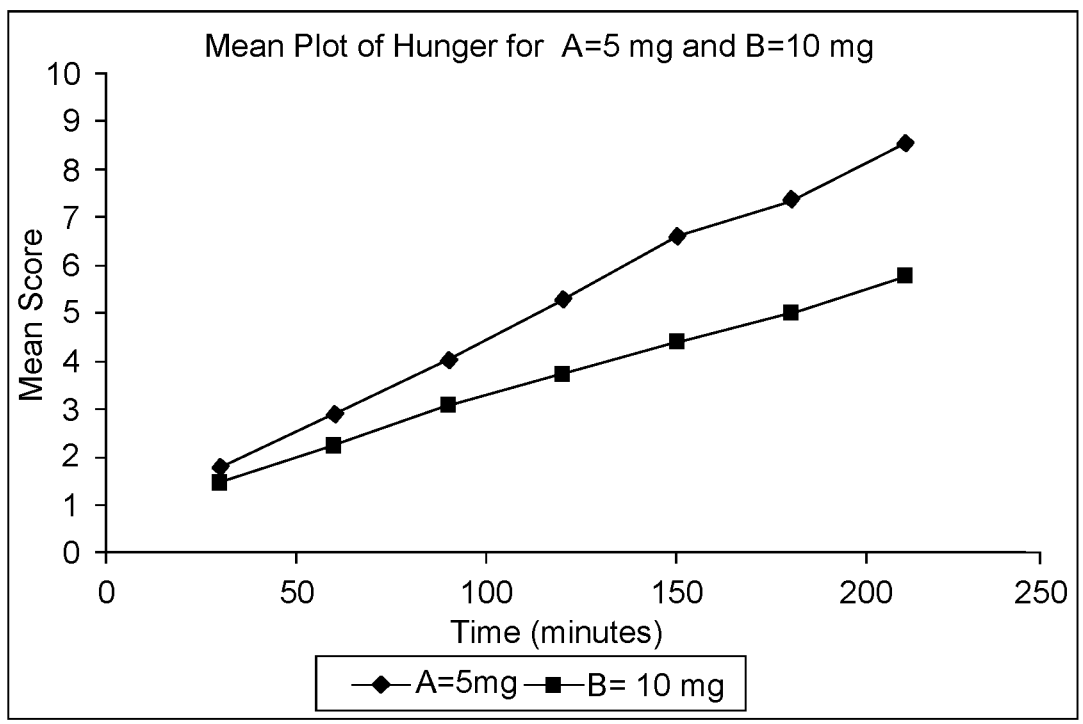
FIG. 4 represents a graph illustrating the Mean plot of hunger scores by treatment A=5 g and B=10 g (N=18) Mean (mm), time (minutes), according to the aspects of present invention.

Mean plot of hunger scores by treatment FIG. 4.

Peak hunger scores were found to be reduced with fenugreek flakes 10 g compared to 5 g.

Fenugreek flakes 10 g resulted in significantly lower AUC (p=0.0006) for hunger scores compared to 5 g.

Hunger scores reduced from 30 minutes post consumption of fenugreek flakes 5 g and 10 g compared to before consumption score at baseline and steadily increased over a period of time in the study.

FIG. 4 represents a graph showing yet another schematic plot illustrating the Mean plot of hunger scores by treatment A=5 g and B=10 g (N=18) Mean (mm), time (minutes).

Example 1.3

Effect of Fenugreek Flakes on Fullness in Healthy Subjects

For fullness, ratings of 0 on the scale=I am not at all full. Ratings of 100=I am totally full.

Figure 5:
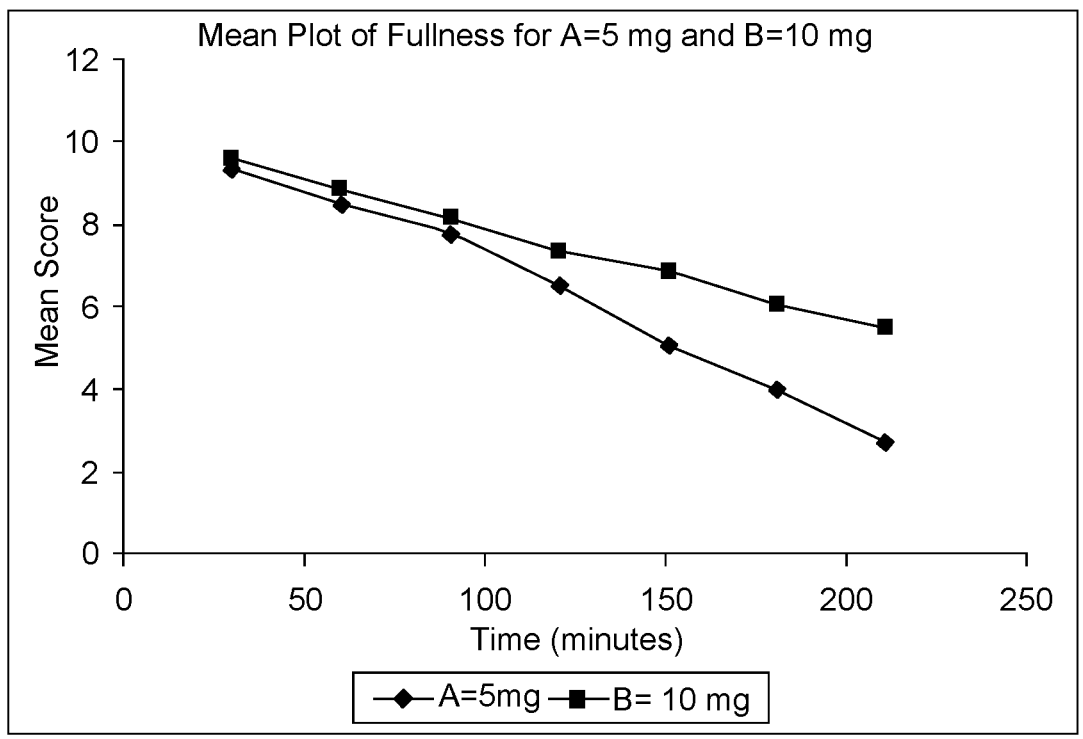
FIG. 5 represents a graph illustrating the Mean plot of fullness scores by treatment A=5 g and B=10 g (N=18) Mean (mm), time (minutes), according to the aspects of present invention.

Mean plot of fullness scores by treatment is presented in FIG. 5.

Peak fullness scores were found to be higher with fenugreek flakes 10 g compared to 5 g.

Fenugreek flakes 10 g resulted in significantly higher AUC (p=0.01) fullness scores compared to 5 g.

Fullness scores increased from 30 minutes post consumption of fenugreek flakes 5 g and 10 g compared to before consumption score at baseline and steadily reduced over a period of time in the study.

FIG. 5 represents a graph showing yet another schematic plot illustrating the Mean plot of fullness scores by treatment A=5 g and B=10 g (N=18) Mean (mm), time (minutes).

Example 1.4

Effect of Fenugreek Flakes on Prospective Food Consumption in Healthy Subjects

For prospective food consumption, ratings of 0 on scales=I can eat nothing at all. Ratings of 100=I can eat a lot.

Figure 6:
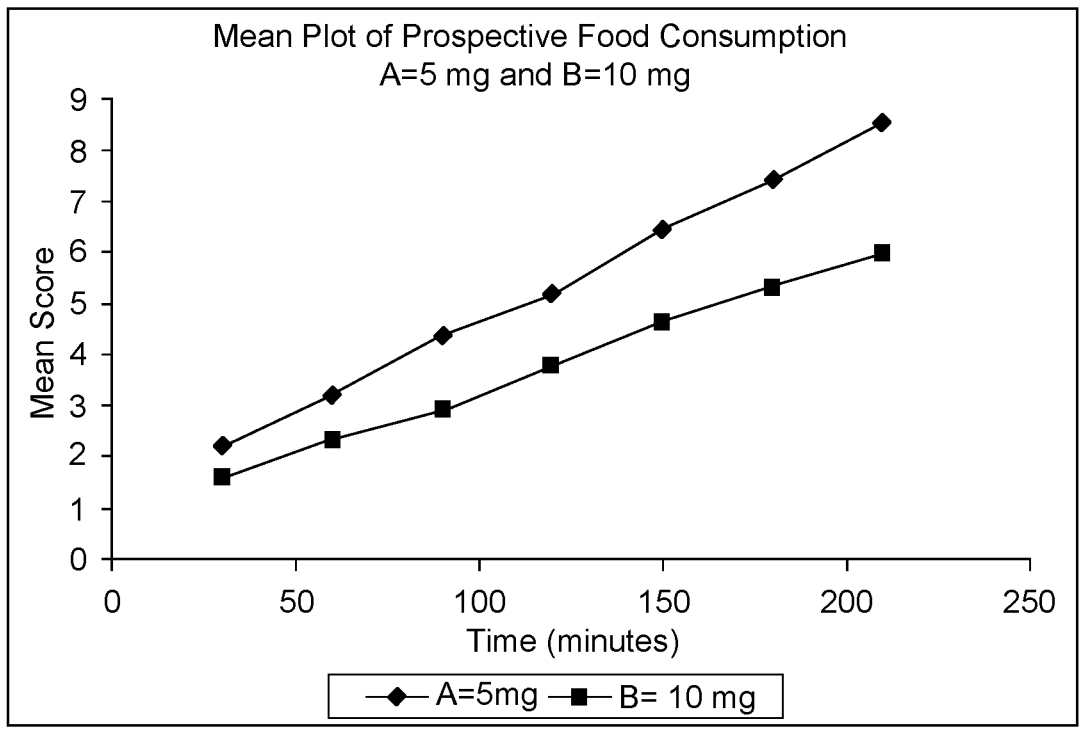
FIG. 6 represents a graph illustrating the Mean plot of prospective food consumption scores by treatment A=5 g and B=10 g (N=18). Mean (mm), time (minutes), according to the aspects of present invention.

Mean plot of prospective food consumption scores by treatment is presented in FIG. 6.

Peak prospective consumption of food scores was found to be lower with fenugreek flakes 10 g compared to 5 g.

Fenugreek flakes 10 g resulted in significantly lower AUC (p<0.008) for prospective food consumption compared to 5 g.

Prospective consumption of food scores reduced from 30 minutes post consumption of fenugreek flakes 5 g and 10 g compared to before consumption score at baseline and steadily increased over a period of time in the study.

FIG. 6 represents a graph showing yet another schematic plot illustrating the Mean plot of prospective food consumption scores by treatment A=5 g and B=10 g (N=18). Mean (mm), time (minutes).

Example 1.5

Effect of Fenugreek Flakes on Desire to Consume Food in Healthy Subjects

Figure 7:
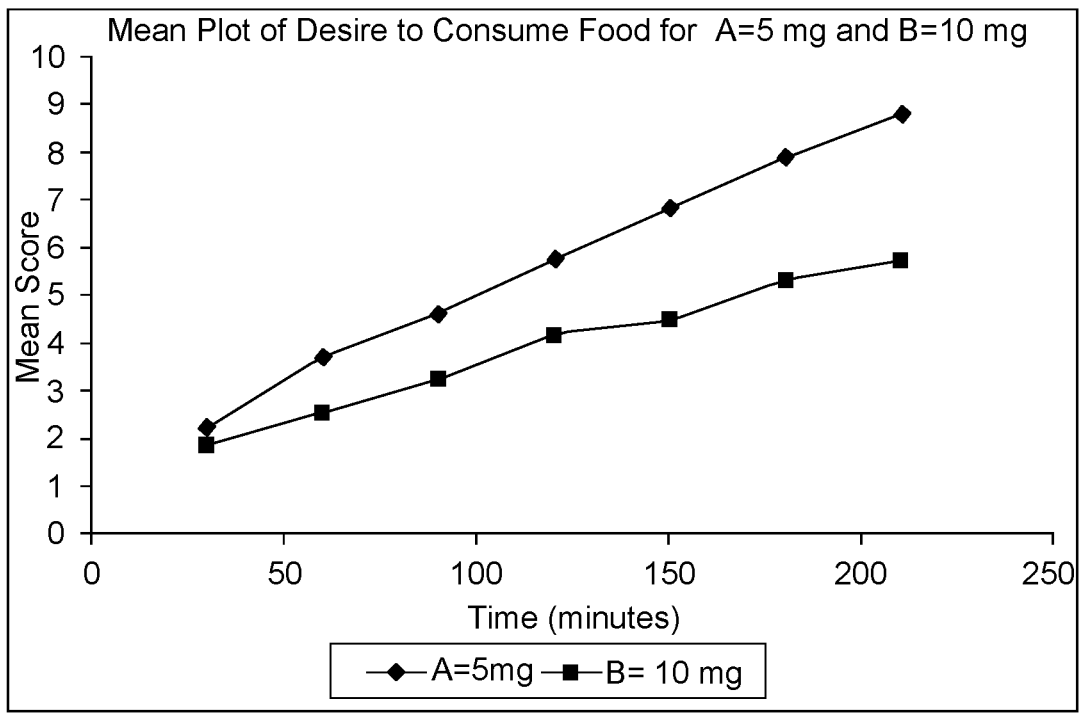
FIG. 7 represents a graph showing the Mean plot of desire to consume food by treatment A=5 g and B=10 g (N=18) Mean (mm), time (mins), according to the aspects of present invention.

Mean plot of desire to consume food scores by treatment is presented in FIG. 7.

FIG. 7 represents a graph showing yet another schematic plot illustrating the Mean plot of desire to consume food by treatment A=5 g and B=10 g (N=18) Mean (mm), time (mins).

Peak desire for consumption of food scores were found to be lower with fenugreek flakes 10 g compared to 5 g.

Fenugreek flakes 10 g resulted in a significantly lower AUC (p=0.0001) for desire after consumption of food scores compared to 5 g.

Desire for consumption of food scores reduced from 30 minutes post consumption of fenugreek flakes 5 g and 10 g compared to before consumption score at baseline and steadily increased over the period of time in the study.

Example 1.6

Effect of Fenugreek Flakes on Palatability in Healthy Subjects

Palatability of the test products were assessed using visual analogue scales. Subjects rated the visual appeal, smell, taste, aftertaste and overall palatability of the test products. Lower scores meant better palatability than higher scores, since on the scale 0=good and 10=bad.

Figure 8:
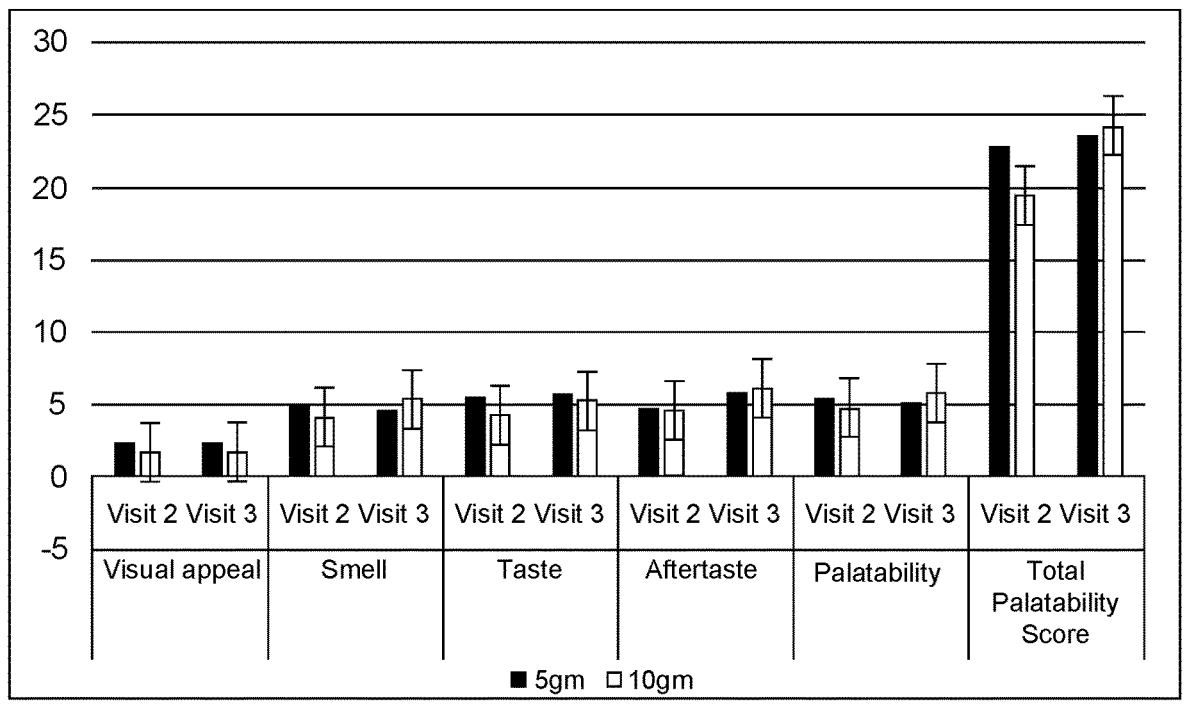
FIG. 8 represents a bar graph illustrating the Mean of palatability score measurements by visit and treatment, according to the aspects of present invention.

Summary of palatability of the fenugreek flakes (5 g or 10 g) are presented in FIG. 8.

FIG. 8 represents a bar graph showing yet another schematic plot illustrating the Mean of palatability score measurements by visit and treatment.

Example 1.7

Effect of Fenugreek Flakes on Blood Parameters in Healthy Subjects

Blood Sugar and Serum Insulin Response Results

A trend of reduction in serum insulin after consumption of fenugreek flakes was observed and the reduction was found to be more with 10 g compared to 5 g. There were no significant changes in glucose levels. The summary of blood glucose and serum insulin is represented in Table 3, FIG. 9 and FIG. 10.

Blood Sugar And Serum Insulin Response Results

Figure 9:
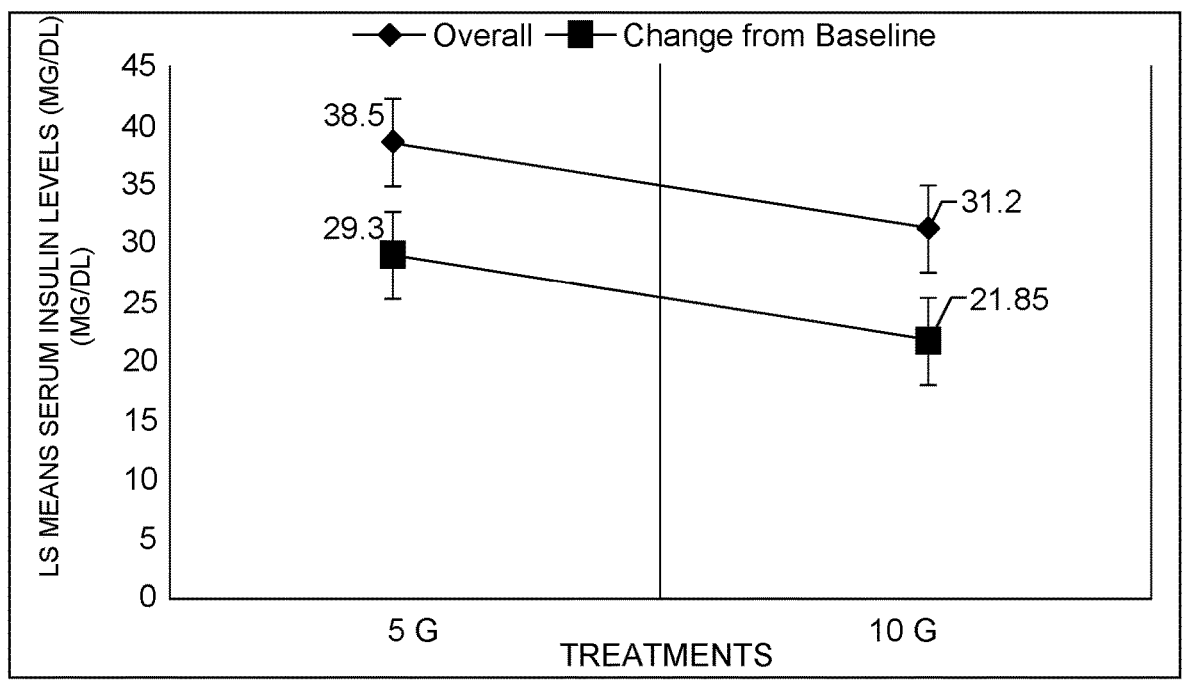
FIG. 9 represents a graph illustrating the LS mean plot of blood glucose levels by treatment A=5 g and B=10 g (N=18), according to the aspects of present invention.
Figure 10:
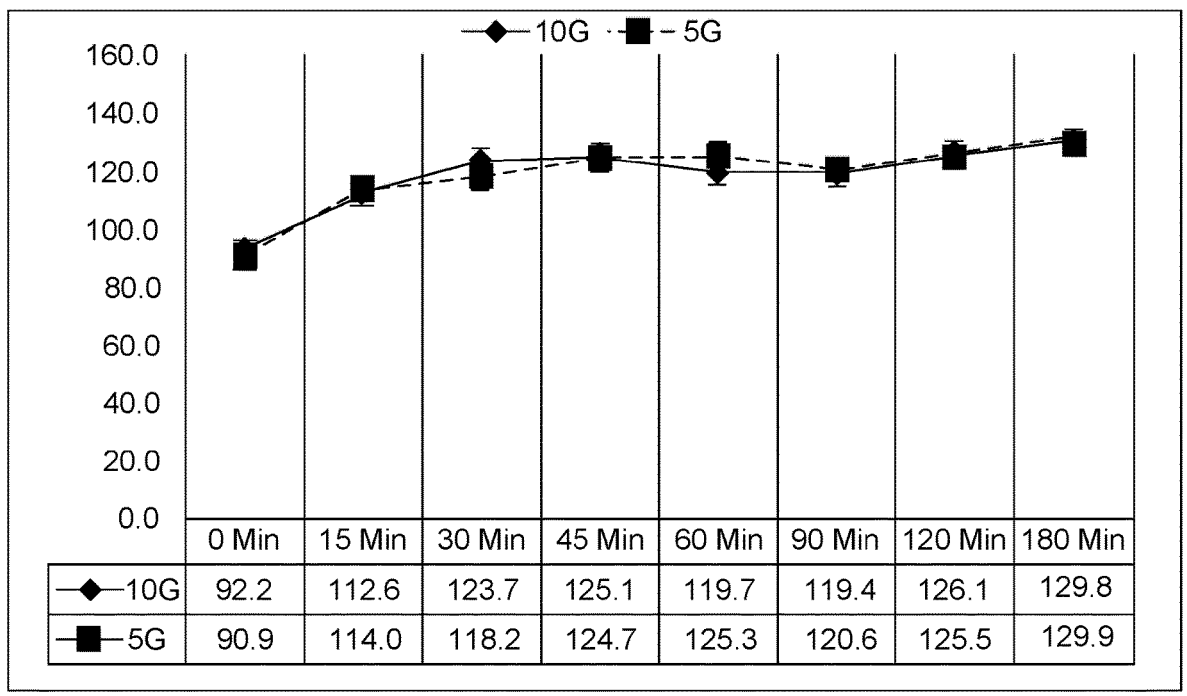
FIG. 10 represents a graph illustrating LS Mean plot of insulin response by treatment A=5 g and B=10 g (N=18), according to the aspect of present invention.

FIG. 9 represents a graph showing yet another schematic plot illustrating the LS mean plot of blood glucose levels by treatment A=5 g and B=10 g (N=18), and FIG. 10 represents a graph showing yet another schematic plot illustrating LS Mean plot of insulin response by treatment A=5 g and B=10 g (N=18).

TABLE 3

| Parameter (Units) | Statistic[a] | Fenugreek Fiber Flakes 5 grams | Fenugreek Fiber Flakes 10 grams | p-value [b] |
|---|---|---|---|---|
| Serum Insulin Response (μU/ml) | LS Mean ± SD | 29.03 ± 21.34 | 21.85 ± 21.34 | 0.03 |
| Blood Glucose Levels (mg/dl) | LS Mean ± SD | 31.63 ± 5.47 | 31.09 ± 5.47 | <0.001 |

[a]Estimated LS Means and Standard Deviation from Repeated Measures ANCOVA model.
[b] P-value is from Overall F-test of Repeated measures ANCOVA.

Conclusions

Fenugreek flakes 5 g and 10 g showed an acceptable safety profile and a positive efficacy trend in improving the satiety in healthy adult subjects. 10 g dose of fenugreek flakes added to a meal increased satiety and fullness and decreased hunger and prospective need of food in VAS scores. This study did not provide evidence that addition of fenugreek flakes to a meal altered carbohydrate metabolism, as no effects were seen on postprandial glycaemia. Insulin response was significantly increased with 10 g fenugreek flakes.

The total palatability scores were found to be better with fenugreek flakes 10 g than 5 g though not significantly. Though the study was a comparison of fenugreek flakes of 5 g versus 10 g, compared to baseline there was a significant change in reported scores of satiety, fullness, hunger, desire to consume food and prospective need of food amongst subjects on fenugreek flakes of 5 g and 10 g. Our study results suggests that fenugreek flakes has a role in the control of food intake in normal individuals who want to use diet as a method to control energy intake through their effects on appetite suppression through feeling of fullness and in food intake.

Example 2

Effect of Two Doses of Fenugreek Flakes (FenuLean®) on Appetite, Body-Weight and Blood Glucose Homeostasis: A Randomized, Double-Blind, Multicenter Three-Arm, Long-Term, Control Study in 100 Healthy Subjects [6]

Dietary fiber, more importantly soluble fiber finds its way into nutrition to be combined with functional foods. The active study products for this study contained FenuLean®-Fenugreek Flakes (FF) 5 g and 10 g. Both FF study products are proprietary products of Bio-gen Extracts Pvt. Ltd., Bangalore, India. The study products are de-fatted and de-bitterized having a high fiber content of ≥50% of which 20% are soluble fibers and 30% are insoluble fibers. In addition, they also have a protein content of ≥20%. The method of extraction and formulation of the product are intended to maximize the health benefits that Fenugreek Flakes (FF) can bring to the consumer at large. Here, the study products were assessed for their effects on appetite scores, secondary changes to blood glucose, change in body weight, BMI and serum insulin levels.

Methods

A double-blind, randomized, three-arm, parallel study to evaluate the efficacy and safety of FenuLean®— Fenugreek Flakes (FF), n=100. The study had two active arms with dosages of 5 g and 10 g of Fenugreek Flakes (FF) versus the third control arm. The study sample population included 100 subjects, 45 subjects in each of the two active arms and 10 subjects in the control arm where no intervention was given. The primary assessment of appetite scores, secondary changes to blood glucose, body weight, BMI and serum insulin levels were measured at baseline and at each of the visits through the duration of study.

Selection of Subjects

Men and women aged 18 to 65 years with body mass index (BMI)≥18 & ≤29.9 kg/m2 with no other metabolic disorders and those who were willing to give informed consent were included in the study. Subjects with hypertension and diabetes and other unstable medical conditions were excluded from the study. Women who were pregnant, breast feeding and planning pregnancy were excluded from the study.

Study Design

The study involved one hundred subjects and was conducted in five visits over a period of forty-five days at two sites in Bangalore, India.

Out of 100 subjects, 10 subjects were designated into the control arm, 45 subjects were in active arm one and 45 subjects were in active arm two.

Subjects who consented to written informed consent forms were enrolled for screening procedures at visit 1.

Subjects were assigned subject screening number (SSN) and underwent eligibility criteria assessment.

After clearing the eligibility criteria, subjects were randomized into control arm and two active arms to receive FenuLean®—Fenugreek Flakes (FF) either 5 g or 10 g in a ratio of 1:1 at visit 2.

The subjects underwent various physical and biochemical tests (that included complete blood count, glycosylated haemoglobin, fasting blood sugar, postprandial blood sugar, serum insulin and urine routine analysis).

Investigational Product

Fenugreek flakes are proprietary products of Bio-gen Extracts Pvt. Ltd. The products were defatted and debitterized. The compound is in the form of flakes. The composition of fenugreek flakes is as shown in Table 1.

Appetite and palatability scores were measured using VAS questionnaires ratings.

Statistical Analysis

Data analyses were performed using the following software: SAS® for Windows 95/NT (Version 9.1 or higher, SAS Institute, Cary, N.C., USA). Area under the curve (AUC) was calculated using trapezoidal rule using WinNonlin® software (Version 5.3). ANCOVA (Analysis of covariance) was performed for the primary variables using baseline as covariates else paired or independent t-test were performed between the treatments. AUC of the VAS satiety scores was calculated using trapezoidal rule. The baseline characteristics were compared among treatment groups. The baseline characteristics which were found to be significant between study groups were accounted in primary analysis model. For continuous variables (age etc.), data was summarized using number of subjects (N), mean, standard deviation (SD), median, minimum and maximum. For categorical variables, data was presented with the number of exposed subjects, number with percentage in various categories of the endpoint, where percentage was based on the exposed subjects. The descriptive variables (gender etc.) were evaluated using Cochran-Mantel-Haenszel test stratified by study center at 0.05 level of significance.

Primary Efficacy Analysis

Changes from baseline for all the primary endpoints such as blood glucose levels, satiety, fullness, hunger, desire to consume food and prospective food consumption VAS score and insulin response were evaluated to assess the functional benefits of fenugreek flakes. Descriptive statistics were performed. Sub group analysis was performed for 2 groups by treatment and the data will be presented in appropriate charts. ANCOVA (Analysis of covariance) was performed for the primary variables using baseline as covariates else paired or independent t-test were performed between the treatments.

Satiety, fullness, hunger, desire to consume food and prospective food consumption Rating Assessment Subjects VAS ratings were converted to a numerical score (0 to 100) from the far-left anchor of the scale. Peak scores (mm) as well as area under curve (AUC, mm*h) was calculated. The cut-off for AUC was 3.5 hours. AUC was calculated using the trapezoidal rule.

For satiety, ratings of 0 on the scales=I am completely empty. Ratings of 100=I cannot eat another bite.

For hunger, ratings of 0=I am not hungry at all. Ratings of 100=I have never been more-hungry.

For fullness, ratings of 0 on the scales=I am not at all full. Ratings of 100=I am totally full.

For desire to consume food, ratings of 0 on the scales=I do have desire to eat. Ratings of 100=I do not have desire to eat food.

For prospective consumption of food, ratings of 0 on the scales=I do like to eat. Ratings of 100=I do not like to eat.

Secondary Efficacy Analysis

Post consumption of the IP the effect of fenugreek fiber flakes on the BMI, body weight, blood glucose and serum insulin and organoleptic properties including visual, taste, smell and palatability of test products at each visit was compared by paired t-tests.

Example 2.1

Figure 11:
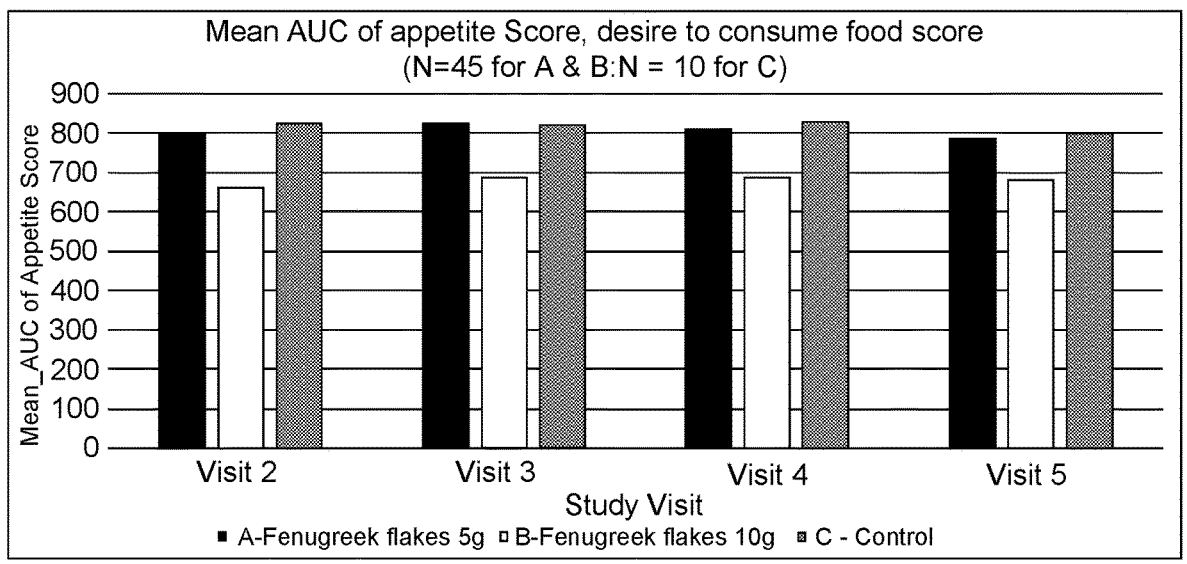
FIG. 11 represents a bar graph showing yet another schematic plot illustrating the Mean AUC of desire to consume food score across visits, according to the aspects of present invention.

Effect of Fenugreek Flakes on Desire to Consume Food Score Across Visits in Healthy Subjects FIG. 11 represents a bar graph showing yet another schematic plot illustrating the Mean AUC of desire to consume food score across visits. In this graph, lower the AUC score better the efficacy and it clearly shows that FF 10 g is better than both FF 5 g & control. This is more or less the same across all the visits.

This was observed to be almost similar in all visits of the study as 15, 30 and 45 days. Lodged fibers (FF 10 g) in the stomach may have delayed the absorption of glucose and thereby delayed the gastric emptying time. Delayed gastric emptying indirectly reduces desire to consume food and this was significantly higher in the FF 10 g group. FF at 5 g had a similar profile like FF 10 g (up to 60 mins), after which there was shift of appetite score to match the control arm throughout the observed time (up to 210 mins). There was no significant change observed in terms of desire to consume the next meal (post 60 mins) in FF 5 g compared to 10 g. However, there was a significant difference in subjects' desire to consume food amongst FF 10 g group in comparison to that of FF 5 g and control groups.

At visits 3, 4 and 5, the profile of FF 5 g matched with that of FF 10 g (for the first 60 minutes) and then matched with the control arm in their response to prospective consumption of food. The mechanism of action of FF (irrespective of the dose) was similar, which was lodging of fibers in the stomach. At the onset of consumption of FF (both strengths), there was a lodging of material in the stomach and delayed absorption of glucose (period of 60 mins) which was quite different from the control arm. A fiber quantity (FF 5 g) may not be sufficient to sustain (up to 210 mins) to produce similar duration of action as FF 10 g. FF 10 g had shown to produce significant reduction in desire to consume food or prospective consumption (though could be due to higher proportion insoluble fibers to soluble fibers) (Please explain this sentence. The relative proportion of soluble & insoluble fibers is the same 20% & 30%). Ratio of higher insoluble fibers to soluble fibers may be required to produce pronounced reduced desire to consume food or prospective consumption of food at Visit 02.

Figure 13:
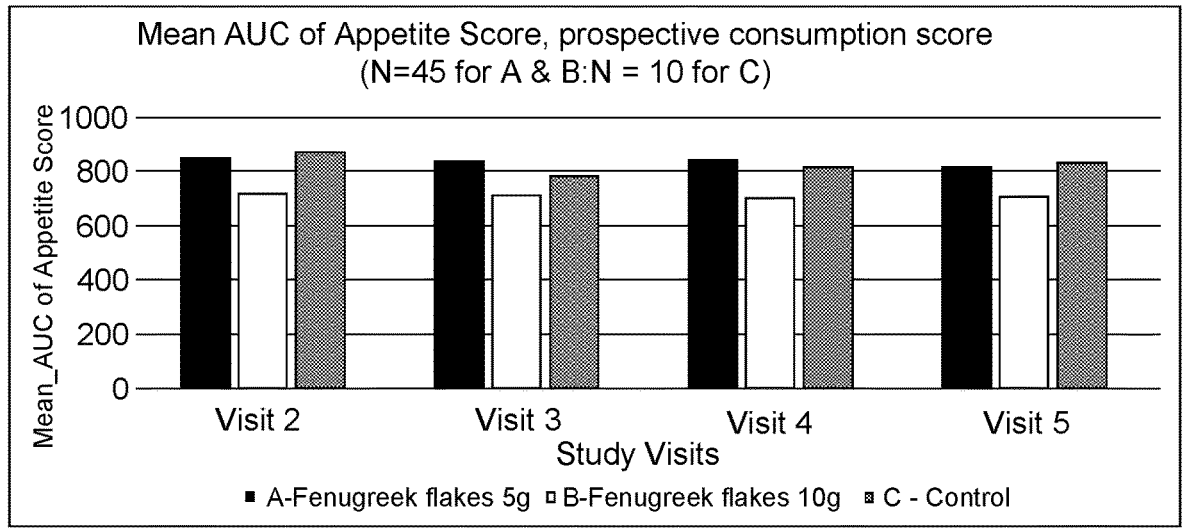
FIG. 13 represents a bar graph showing yet another schematic plot illustrating the Mean AUC of prospective consumption score across visits, according to the aspects of present invention.

Subjects treated with FF 10 g significantly reduced prospective need for food (FIG. 13). When measured over 210 mins (3.5 hours); amount of food lodged in the stomach had not emptied in 3.5 hours (post consumption) with FF 10 g. This was observed on subjects treated throughout the study and when measured specifically on day 15, 30 and 45. This was quite different from that seen on subjects with FF 5 g and control groups. Subjects on FF 5 g showed prospective food consumption similar to FF 10 g (for the first 60 mins), while for the rest of the time until 210 mins, it had almost matched that of the control.

Example 2.2

Effect of Fenugreek Flakes on Hunger Score Across Visits in Healthy Subjects

Figure 12:
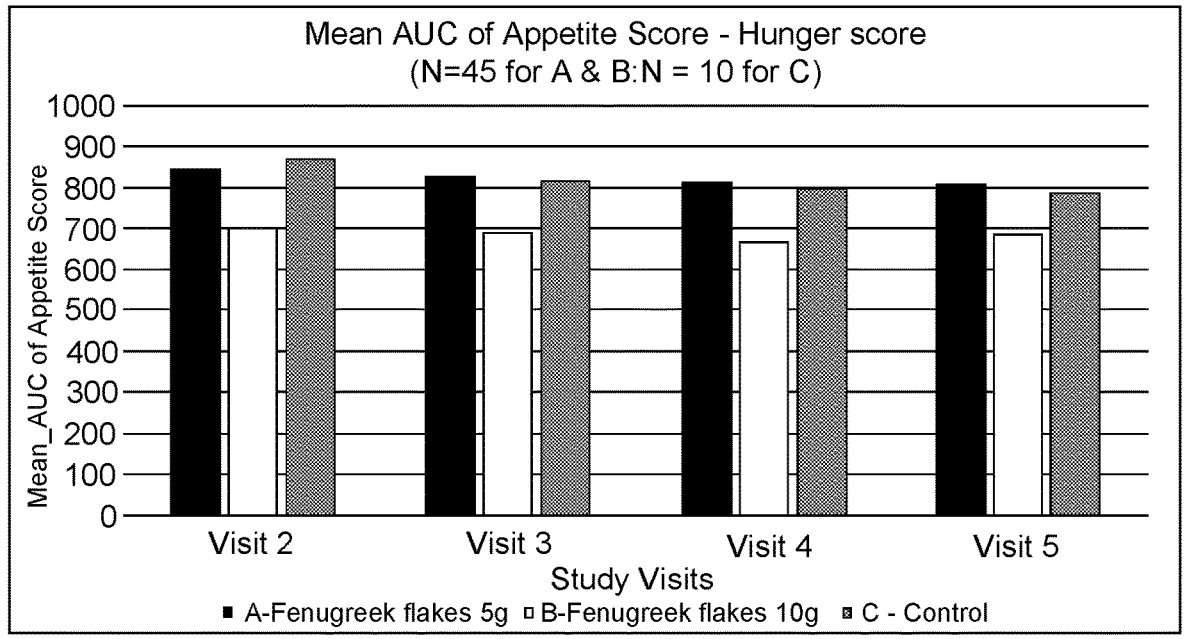
FIG. 12 represents a bar graph showing yet another schematic plot illustrating the Mean AUC of hunger score across visits, according to the aspects of present invention.

FIG. 12 represents a bar graph showing yet another schematic plot illustrating the Mean AUC of hunger score across visits. In this graph, lower the AUC score better the efficacy and it clearly shows that FF 10 g is better than both FF 5 g & control. This is more or less the same across all the visits. Hunger scores have no bearing on the visits and it remained unchanged.

Example 2.3

Effect of Fenugreek Flakes on Prospective Consumption Score Across Visits in Healthy Subjects FIG. 13 represents a bar graph showing yet another schematic plot illustrating the Mean AUC of prospective consumption score across visits. In this graph, lower the AUC score better the efficacy and it clearly shows that FF 10 g is better than both FF 5 g & control. This is more or less the same across all the visits. Prospective need to consume food has not much changed across the visits However, it is interesting to note that FF 5 g is almost similar to control.

Example 2.4

Figure 14:
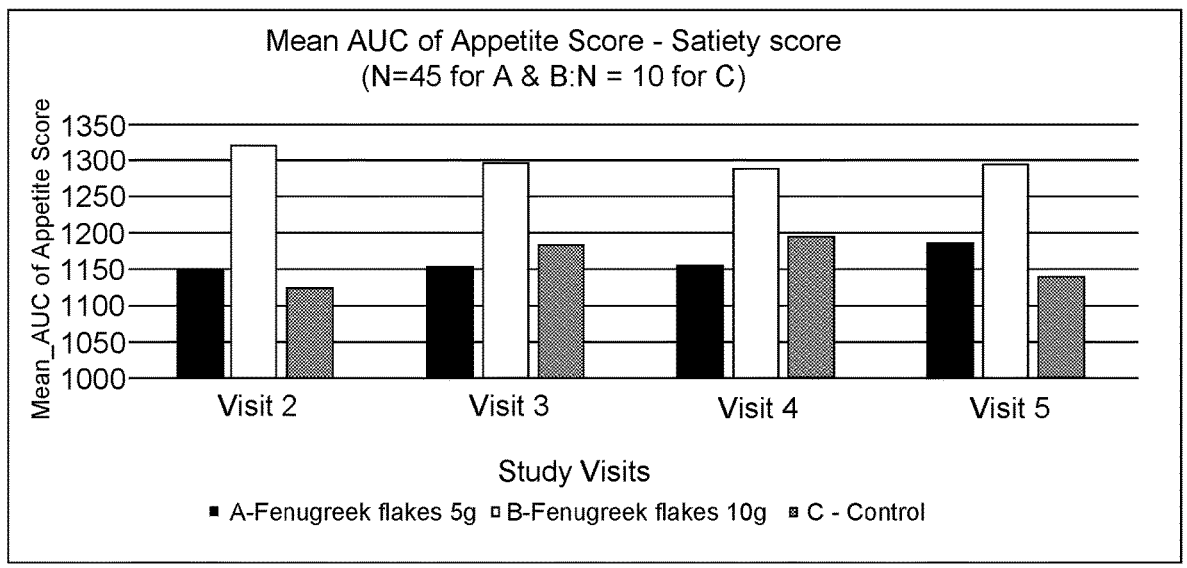
FIG. 14 represents a bar graph showing yet another schematic plot illustrating the Mean AUC of satiety score, according to the aspects of present invention.

Effect of Fenugreek Flakes on Mean AUC of Satiety Score Across Visits in Healthy Subjects FIG. 14 represents a bar graph showing yet another schematic plot illustrating the Mean AUC of satiety score. In this graph, higher the AUC score better the efficacy and it clearly shows that FF 10 g is better than both FF 5 g & control. Satiety scores are higher amongst subjects who has consumed FF 10 g and it is seen across the visits. However, there are not many changes that can be observed amongst subjects who has consumed 5 g when compared control in the different visits.

Example 2.5

Figure 15:
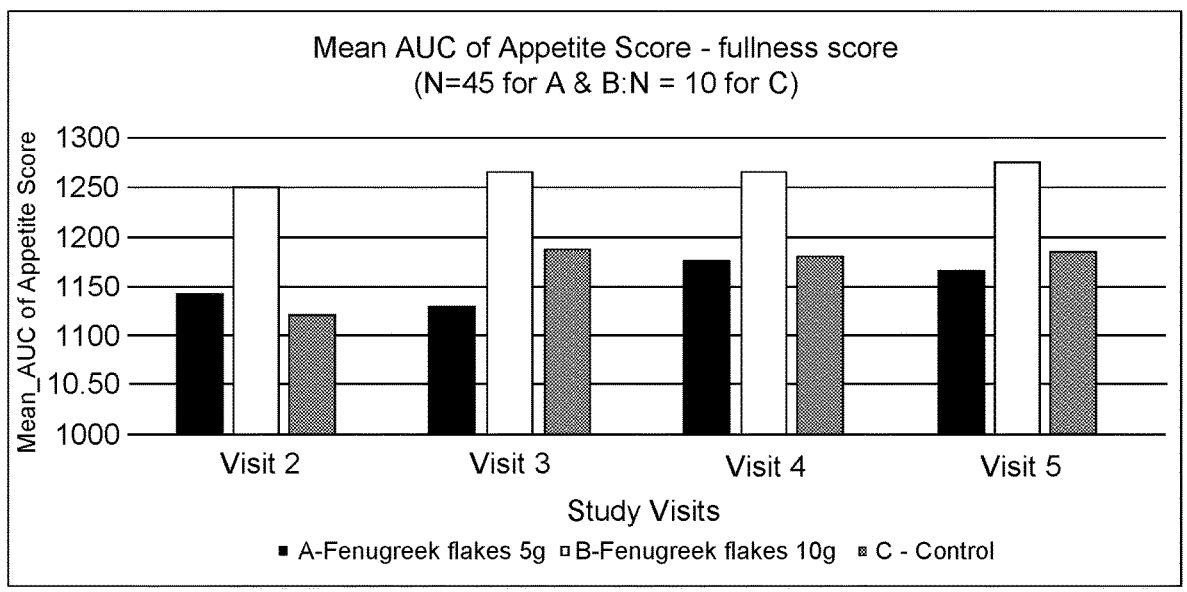
FIG. 15 represents a bar graph showing yet another schematic plot illustrating the Mean AUC of fullness score across visits, according to the aspects of present invention.

Effect of Fenugreek Flakes on Mean AUC of Fullness Score Across Visits in Healthy Subjects FIG. 15 represents a bar graph showing yet another schematic plot illustrating the Mean AUC of fullness score across visits. In this graph, higher the AUC score better the efficacy and it clearly shows that FF 10 g is better than both FF 5 g & control. This is more or less the same across all the visits. Feeling of fullness is not significantly observed in control or FF 5 g dose.

Example 2.6

Figure 16:
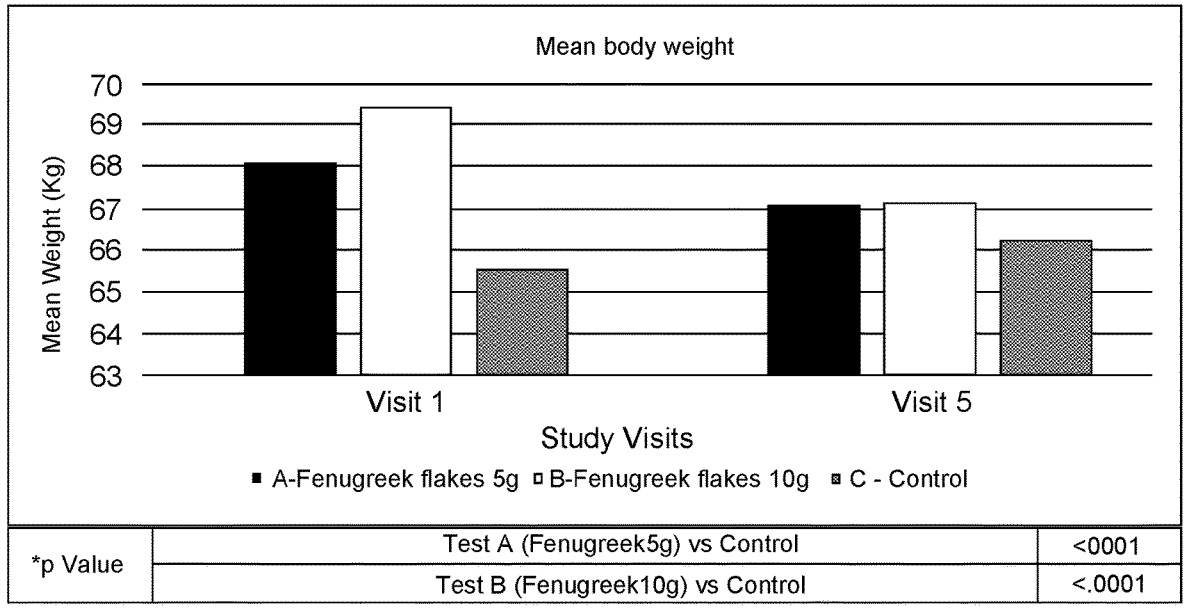
FIG. 16 represents a bar graph showing yet another schematic plot illustrating the Mean weight reduction in the treatment groups and control over a period of 45 days, according to the aspects of present invention.

Effect of Fenugreek Flakes on Mean Weight Reduction in the Treatment Groups and Control Subjects FIG. 16 represents a bar graph showing yet another schematic plot illustrating the Mean weight reduction in the treatment groups and control over a period of 45 days. In the above graph when compared to control in Visit 1 (FF 5 g & 10 g), at Visit 5 (FF 5 g & 10 g) body weight is significantly reduced (P<0.001) over a period of 45 days. There is a significant increase in body weight amongst control which clearly demonstrates effect of FF 5 g and 10 g on body weight and how appetite scores have some significant effect on the changes in body weight and metabolic parameters.

In the above graph when compared to control in Visit 1 (FF 5 g & 10 g), at Visit 5 (FF 5 g & 10 g) body weight is significantly reduced (P<0.001) over a period of 45 days. There is a significant increase in body weight amongst control which clearly demonstrates effect of FF 5 g and 10 g on body weight and how appetite scores have some significant effect on the changes in body weight and metabolic parameters.

Example 2.7

Figure 17:
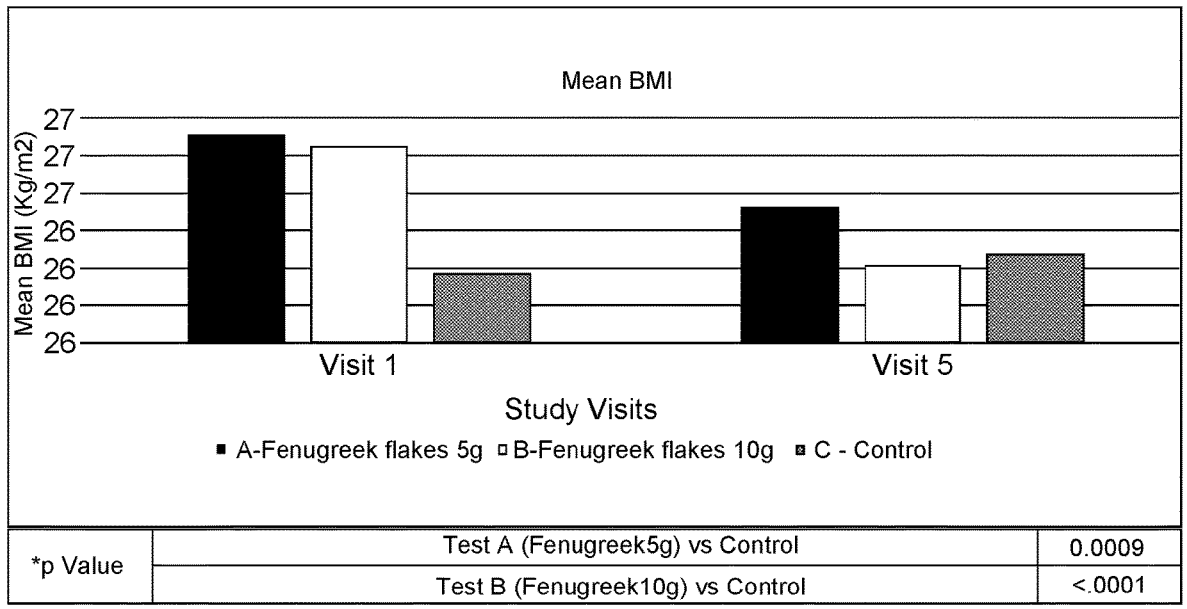
FIG. 17 represents a bar graph showing yet another schematic plot illustrating the Change of BMI in the treatment groups and control over a period of 45 days, according to the aspects of present invention.

Effect of Fenugreek Flakes Change of BMI in the Treatment Groups and Control Subjects FIG. 17 represents a bar graph showing yet another schematic plot illustrating the Change of BMI in the treatment groups and control over a period of 45 days. In the above graph when compared to control in Visit 1 (FF 5 g & 10 g), at Visit 5 (FF 5 g & 10 g) BMI is significantly reduced (P=0.0009 & P<0.0001) over a period of 45 days. There is a significant increase in BMI amongst control which clearly demonstrates effect of FF 5 g and 10 g on BMI and how appetite scores have some significant effect on the changes in body metabolic processes.

Body weight and body mass index (BMI) in Fenugreek 5 g, 10 g and the control arms were summarized by visit and treatment. Mean changes in body weight and BMI from baseline to end of treatment (EOT) were summarized and compared between treatments using independent t-test with 5% level of significance. Data suggested that if the study was exposed to a longer treatment period, even further significant changes may be observed in body weight and BMI. In the control group, there was a significant increase in body weight. This clearly demonstrates the effect of FF 5 g and 10 g on BMI, especially acting through reduced appetite scores that could play a large part causing changes in the metabolic processes of the body. These indicators provided potential insight to look at this effect in long term consumption of FF.

The above graph shows the effect of FF in comparison to control groups on the blood levels of glucose both at baseline and in Visit 5. Fasting blood glucose (FBS) is reduced significantly in FF 5 g (P=0.0001) and FF 10 g (P<0.0001) between the two visits on Visit 1 and Visit 5. This difference is not observed in the control group when the measures of FBS were done on Visit 1 and Visit 5. The effect of FF on FBS is profoundly observed in higher doses compared to lower doses, which also establishes the theory of dose dependency in controlling glucose levels. FF (5 g/10 g) is able to show reduction in fasting glucose and some inherent effects on glucose metabolism which is reported in literature.

Table 4: Fasting Blood Sugar (FBS) & Post Prandial Blood Sugar (PPBS) in the treatment groups and control over visits (1 vs 5).

TABLE 4

|  | Baseline FBS (mg/dL) | Baseline PPBS (mg/dL) | Visit 5 FBS (mg/dL) | Visit 5 PPBS (mg/dL) |
|---|---|---|---|---|
| Treatment-A (Fenugreek 5 g) | | | | |
| N | 45 | 45 | 45 | 45 |
| Mean | 90.36 | 111.867 | 82.82 | 103.311 |
| SD | 10.11 | 13.534 | 7.29 | 16.789 |
| *p Value (Baseline vs V5) | | | 0.0001 | 0.0092 |
| Treatment-B (Fenugreek 10 g) | | | | |
| N | 45 | 45 | 45 | 45 |
| Mean | 92.82 | 114.156 | 81.56 | 99.489 |
| SD | 10.83 | 18.211 | 6.77 | 15.250 |
| *p Value (Baseline vs V5) | | | <.0001 | <.0001 |
| Treatment-C (Control) | | | | |
| N | 10 | 10 | 10 | 10 |
| Mean | 94.40 | 111.600 | 87.40 | 107.700 |
| SD | 9.78 | 15.672 | 10.20 | 20.407 |
| *p Value (Baseline vs V5) | | | 0.1346 | 0.6375 |

*ANOVA Analysis

Table 4. Shows the effect of FF in comparison to control groups on the blood levels of glucose both at baseline and in Visit 5. Fasting blood glucose (FBS) is reduced significantly in FF 5 g (P=0.0001) and FF 10 g (P<0.0001) between the two visits on Visit 1 and Visit 5. This difference is not observed in the control group when the measures of FBS were done on Visit 1 and Visit 5. The effect of FF on FBS is profoundly observed in higher doses compared to lower doses, which also establishes the theory of dose dependency in controlling glucose levels. FF (5 g/10 g) is able to show reduction in fasting glucose and some inherent effects on glucose metabolism which is reported in literature.

Post prandial blood glucose (PPBS) is reduced significantly in FF 5 g (P=0.0092) and FF 10 g (P<0.0001) between the two visits on Visit 1 and Visit 5. This difference is not observed in the control group when the measures of PPBS were done on Visit 1 and Visit 5. PPBS is an important indicator to assess surge of glucose levels (changes post consumption of a meal) and its effect on serum insulin levels 10. Effect of FF on PPBS (like FBS) is dose dependent and at higher strength (FF 10 g) produced significant reduction in PPBS levels. All the subjects in the study had impaired glycosylated haemoglobin who may have had higher BMI (>25) with no other metabolic aberrations. This also establishes the fact that these actions are beneficial and shows how the reduction in glucose reabsorption and appetite scores is correlated. Effect on PPBS is absent in the control arm of the study across the visits.

TABLE 5

|  | Baseline Serum insulin (µU/ml) | Baseline Post meal (at 120 min) serum insulin (µU/ml) | Visit 5 Serum insulin (µU/ml) | Visit 5 Past meal (at 120 min) serum insulin (µU/ml) |
|---|---|---|---|---|
| Treatment-B (Fenugreek 10 g) | | | | |
| N | 45 | 45 | 45 | 45 |
| Mean | 16.29 | 30.447 | 21.42 | 32.362 |
| SD | 10.73 | 18.931 | 13.25 | 27.195 |
| *p Value (Baseline vs V5) | | | 0.0465 | 0.6991 |
| Treatment-A (Fenugreek 5 g) | | | | |
| N | 45 | 45 | 45 | 45 |
| Mean | 19.71 | 29.640 | 20.76 | 33.749 |
| SD | 17.75 | 19.705 | 18.06 | 29.769 |
| *p Value (Baseline vs V5) | | | 0.7822 | 0.4421 |
| Treatment-C (Control) | | | | |
| N | 10 | 10 | 10 | 10 |
| Mean | 14.24 | 45.940 | 15.36 | 53.550 |
| SD | 10.74 | 28.848 | 10.34 | 41.225 |
| *p Value (Baseline vs V5) | | | 0.8149 | 0.6382 |

Table 5. Shows effect of treatment and control arm on serum insulin at baseline (both at 1 and 120 mins) at Visit 1 and Visit 5. There are no significant differences observed in serum insulin from visit 1 and 5. Serum insulin is not impacted by treatment or by time (pre and post consumption of FF). Insulin changes and its impact on glucose levels are important today in dietary modifications especially in non-diabetes subjects with a BMI of over 25.

Conclusion

No other studies have been established to assess the ability of FF to modulate appetite scores and compare appetite scores over a period of time with control in a large sample size (~100 subjects). Clinical investigators evaluated the ability of the FF (as key fibers) in modulating or impacting the appetite scores as primary outcome measures in a randomized, multi-center, parallel group, long term, prospective double-blind clinical study. This study established the fact that supplementation with FF under normal dietary conditions (without any restrictions) decreased energy intake through reduction in hunger, feeling of fullness and feeling of satiety at the end of forty-five days of supplementation or treatment. These parameters were part of the quantifiable postprandial appetite scores which were essential to assess the quality and impact of quantity of FF in the study.

This also established the fact these actions were beneficial and exhibited how glucose reabsorption, reduction and appetite scores correlated to the carbohydrate metabolism.

One of the important factors to assess the effect of insulin with respect to food enriched with FF and its action on glucose metabolism. Significant changes were observed in about forty-five days with FF finding some beneficial effect on the dietary and nutritional value as established in previous studies. There was a clear linear relationship established of dose dependent effect of FF on fasting blood sugar, post prandial glucose, appetite score, weight loss and BMI.

According to a further non-limiting exemplary aspect of the present invention can be incorporated into food products, such as cookies, cereals, crackers, doughnuts, bagels, biscuits, pasta, bread, baked goods, pizza dough, juices, gravies, sauces, salads, and candies.

According to a non-limiting exemplary aspect of the present invention can be used for the development of diet plan and nutritional supplements.

Merely for illustration, only representative number/type of graph, chart, block, and sub-block diagrams were shown. Many environments often contain many more block and sub-block diagrams or systems and sub-systems, both in number and type, depending on the purpose for which the environment is designed.

While specific embodiments of the invention have been shown and described in detail to illustrate the inventive principles, it will be understood that the invention may be embodied otherwise without departing from such principles.

Reference throughout this specification to "one embodiment", "an embodiment", or similar language means that a particular feature, structure, or characteristic described in connection with the embodiment is included in at least one embodiment of the present invention. Thus, appearances of the phrases "in one embodiment", "in an embodiment" and similar language throughout this specification may, but do not necessarily, all refer to the same embodiment.

It should be understood that the figures and/or screen shots illustrated in the attachments highlighting the functionality and advantages of the present invention are presented for example purposes only. The present invention is sufficiently flexible and configurable, such that it may be utilized in ways other than that shown in the accompanying figures.

The foregoing description of the specific embodiments fully discloses the general nature of the embodiments herein that others can, by applying existing knowledge, readily modify and/or adapt for various applications such specific embodiments without departing from the generic concept, and, therefore, such changes, modifications and adaptations should and are intended to be comprehended within the meaning and range of equivalents of the disclosed embodiments.

It is understood that the phraseology or terminology used herein is for the purpose of explanation and not of limitation. It is therefore, the embodiments in this invention have been described in terms of preferred embodiments, those skilled in the art will recognize that the embodiments herein can be practiced with modification within the spirit and scope of the embodiments as described herein.

With respect to the use of substantially any plural and/or singular terms herein, those having skill in the art can interpret from the plural to the singular and/or from the singular to the plural as is appropriate to the context and application. The singular/plural permutations may be expressly set forth herein for the purpose of explanation.

The use of the expression "at least" or "at least one" suggests the use of one or more elements or ingredients or quantities, as the use may be in the embodiment of the invention to achieve one or more of the desired results. Any discussion of materials, devices, documents, acts, articles and the like that has been included in this specification is solely for the purpose of offering a context for the invention. It is not to be consider as an admission that any or all of these matters form a part of the prior art base or were common general knowledge in the field relevant to the invention as it existed anywhere before the priority date of this application.

It should be understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCE

1) Slavin J L. Position of the American Dietetic Association: health implications of dietary fiber. J Am Diet Assoc. 2008; 108 (10):1716-31.
2) Byrne C S, Chambers E S, Morrison D J, Frost G. The role of short chain fatty acids in appetite regulation and energy homeostasis. International Journal of Obesity. 2015; 39 (9):1331-1338.
3) Maskarinec G, Takata Y, Pagano I, et al. Trends and dietary determinants of overweight and obesity in a multiethnic population. Obesity (Silver Spring). 2006; 14 (4):717-26.
4) Flint A, Raben A, Blundell J E, Astrup A. Reproducibility, power and validity of visual analogue scales in assessment of appetite sensations in single test meal studies. Int J Obes Relat Metab Disord. 2000; 24 (1):38-48.
5) Chandra J R, Dasegowda S M, Vrushabaiah G K, Shivayogi P, Bopanna K. Effect of fenugreek fiber flakes on appetite scores and glucose homeostasis in healthy subjects. International Journal of Medical and Health Research. 2018; 4 (10): 14-21.
6) Mehkri S, Ambarish C, Madankumar B J, Shivayogi P, Bopanna K. Effect of two doses of Fenugreek Flakes (FenuLean™) on appetite, body-weight and blood glucose homeostasis: A randomized, double-blind, multicenter, three-arm, long-term, control study in 100 healthy subjects. International Journal of Medical Science and Clinical Research. 2019; 1 (4): 07-14.

What is claimed is:

1. A method for reducing fasting blood glucose, postprandial blood glucose, body weight and BMI in a subject in need thereof comprising administering an effective amount of a composition that comprises:
(A) a *Trigonella foenum-grecum* preparation comprising protein ranging from 15% to 40% w/w, L-Arginine from 0.1% to 3%, L-Tryptophan from 0.1% to 2%, L-Leucine from 0.1% to 2%, and L-Isoleucine from 0.1% to 1.5%, and fiber containing resistant starch ranging from 25% to 65% w/w comprising galactomannans from 10% to 26% w/w, and insoluble fiber from 15% to 39% w/w; and
(B) one or more additives selected from a group comprising gum, granulating agents, binding agents, lubricating agents, disintegrating agents, sweetening agents, coloring agents, flavoring agents, coating agents, plasticizers, preservatives, suspending agents, emulsifying agents, antioxidants, surfactants, viscosity enhancers, plant cellulosic materials, solvents, glidants, anti-adherents, anti-static agents, preservatives, suspending agents, and spheronization agents;

wherein said administering a daily dosage of 5 to 10 grams of the composition for 45 days achieves a reduction in:
(i) fasting blood glucose of 8% or more,
(ii) postprandial blood glucose of 7% or more,
(iii) body weight of 1% or more, and
(iv) BMI of 1% or more.

2. The method of claim 1, wherein the composition is administered orally.

3. The method of claim 1, wherein the composition is gluten-free.

4. The method of claim 1, wherein the composition is in the form of flakes comprising a particle size of between 0.4 mm to 6 mm, with a preferable size of 3 mm to 5 mm.

5. The method of claim 1, wherein the administering of an effective amount of a composition reduces hunger, creates a feeling of fullness and satiety in the subject.

6. A method for reducing fasting blood glucose, postprandial blood glucose, body weight and BMI in a subject in need thereof comprising administering an effective amount of a composition that comprises:
(A) a *Trigonella foenum-grecum* preparation comprising protein ranging from 15% to 40% w/w, L-Arginine from 0.1% to 3%, L-Tryptophan from 0.1% to 2%, L-Leucine from 0.1% to 2%, and L-Isoleucine from 0.1% to 1.5%, and fiber containing resistant starch ranging from 25% to 65% w/w comprising galactomannans from 10% to 26% w/w, and insoluble fiber from 15% to 39% w/w; and
(B) one or more additives selected from a group comprising gum, granulating agents, binding agents, lubricating agents, disintegrating agents, sweetening agents, coloring agents, flavoring agents, coating agents, plasticizers, preservatives, suspending agents, emulsifying agents, antioxidants, surfactants, viscosity enhancers, plant cellulosic materials, solvents, glidants, anti-adherents, anti-static agents, preservatives, suspending agents, and spheronization agents;
wherein the administering is done orally with a minimum daily dosage of 5 grams for a minimum period of 45 days; and
monitoring of the subjects shows a reduction in fasting blood glucose of 8% or more, a reduction in postprandial glucose of 7% or more, a reduction in body weight of 1% or more, and a reduction in BMI of 1% or more within 45 days.

7. The method of claim 6, wherein the composition is gluten-free.

8. The method of claim 6, wherein the composition is in the form of flakes comprising a particle size of between 0.4 mm to 6 mm, with a preferable size of 3 mm to 5 mm.

* * * * *